(12) United States Patent
Matsumoto et al.

(10) Patent No.: US 9,698,352 B2
(45) Date of Patent: *Jul. 4, 2017

(54) AMINE COMPOUND AND USE THEREOF

(71) Applicant: TOSOH CORPORATION, Yamaguchi (JP)

(72) Inventors: Naoki Matsumoto, Yamaguchi (JP); Takanori Miyazaki, Yamaguchi (JP); Ryohei Takahashi, Yamaguchi (JP)

(73) Assignee: TOSOH CORPORATION, Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/430,355

(22) PCT Filed: Sep. 26, 2013

(86) PCT No.: PCT/JP2013/076097
§ 371 (c)(1),
(2) Date: Mar. 23, 2015

(87) PCT Pub. No.: WO2014/050982
PCT Pub. Date: Apr. 3, 2014

(65) Prior Publication Data
US 2015/0243901 A1    Aug. 27, 2015

(30) Foreign Application Priority Data

Sep. 27, 2012 (JP) ................. 2012-214844
Jun. 6, 2013 (JP) ................. 2013-119485

(51) Int. Cl.
| | | |
|---|---|---|
| C07D 405/04 | (2006.01) |
| C07D 409/04 | (2006.01) |
| C07D 409/14 | (2006.01) |
| H01L 51/00 | (2006.01) |
| C07D 405/14 | (2006.01) |
| C09K 11/06 | (2006.01) |
| H05B 33/14 | (2006.01) |
| H01L 51/50 | (2006.01) |

(52) U.S. Cl.
CPC ........ *H01L 51/0061* (2013.01); *C07D 405/04* (2013.01); *C07D 405/14* (2013.01); *C07D 409/04* (2013.01); *C07D 409/14* (2013.01); *C09K 11/06* (2013.01); *H01L 51/006* (2013.01); *H01L 51/0072* (2013.01); *H01L 51/0073* (2013.01); *H01L 51/0074* (2013.01); *H05B 33/14* (2013.01); *C09K 2211/1022* (2013.01); *C09K 2211/1029* (2013.01); *C09K 2211/1088* (2013.01); *C09K 2211/1092* (2013.01); *H01L 51/0052* (2013.01); *H01L 51/5012* (2013.01); *H01L 51/5056* (2013.01); *H01L 51/5088* (2013.01)

(58) Field of Classification Search
None
See application file for complete search history.

(56) References Cited

U.S. PATENT DOCUMENTS

| | | | |
|---|---|---|---|
| 9,172,045 B2 * | 10/2015 | Matsumoto | .......... C07D 209/86 |
| 2009/0017330 A1 | 1/2009 | Iwakuma et al. | |
| 2009/0017331 A1 | 1/2009 | Iwakuma et al. | |
| 2009/0167162 A1 | 7/2009 | Lin et al. | |
| 2011/0278552 A1 | 11/2011 | Numata et al. | |
| 2012/0203010 A1 | 8/2012 | Matsumoto et al. | |

FOREIGN PATENT DOCUMENTS

| | | |
|---|---|---|
| CN | 101669226 | 3/2010 |
| JP | 2007-126439 | 5/2007 |

(Continued)

OTHER PUBLICATIONS

"Journal of Applied Physics", 2004, pp. 7798, vol. 95.

(Continued)

*Primary Examiner* — Nyeemah A Grazier
(74) *Attorney, Agent, or Firm* — Greenblum & Bernstein, P.L.C.

(57) ABSTRACT

To provide a novel amine compound which is especially suitable for a hole transport material for organic EL devices, and an organic EL device which employs such an amine compound and is excellent in the driving voltage, luminous efficiency and device lifetime An amine compound represented by the formula (1):

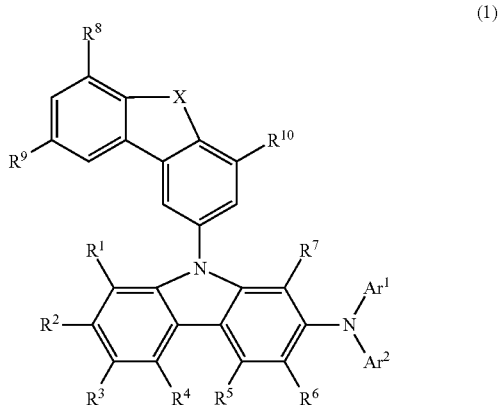

(1)

(wherein X is a sulfur atom or an oxygen atom, each of $R^1$ to $R^{10}$ which are independent of one another, is a hydrogen atom, a deuterium atom or a phenyl group, and each of $Ar^1$ and $Ar^2$ which are independent of each other, is a $C_{6-18}$ aromatic hydrocarbon group, a dibenzothienyl group or a dibenzofuranyl group, which, each independently, may have a substituent consisting of a methyl group, a methoxy group, a dibenzothienyl group, a dibenzofuranyl group or a 9-carbazolyl group.).

6 Claims, No Drawings

(56) References Cited

FOREIGN PATENT DOCUMENTS

| JP | 2011-001349 | 1/2011 |
|---|---|---|
| JP | 2011-509247 | 3/2011 |
| JP | 2011-088835 | 5/2011 |
| JP | 2011-231025 | 11/2011 |
| JP | 2012-144515 | 8/2012 |
| KR | 10-2009-0129799 | 12/2009 |
| WO | 2008-156105 | 12/2008 |
| WO | 2009/008100 | 1/2009 |
| WO | 2011/122132 | 10/2011 |
| WO | 2011/125680 | 10/2011 |
| WO | 2012/077520 | 6/2012 |
| WO | 2013/039073 | 3/2013 |

OTHER PUBLICATIONS

Search report from PCT/JP2013/076097, mail date is Oct. 22, 2013.
International Report on Patentability in PCT/JP2013/076097, mail date is Mar. 31, 2015.

\* cited by examiner

AMINE COMPOUND AND USE THEREOF

TECHNICAL FIELD

The present invention relates to a novel 9-dibenzothienyl or 9-dibenzofuranyl-2-aminocarbazole compound and an organic EL device employing it.

BACKGROUND ART

An organic EL device is a surface emitting device having an organic thin film sandwiched by a pair of electrodes, and it has characteristics such as being thin and light in weight, having a wide viewing angle, having high speed responsiveness, etc. and thus is expected to be applied to various display devices. Further, recently, its practical application to e.g. the display of a mobile phone has partly started. Such an organic EL device is one which utilizes light emitted at the time when holes injected from an anode and electrons injected from a cathode are recombined in a luminescent layer, and its prevailing structure is a multilayer laminate type having a hole transport layer, a luminescent layer, an electron transport layer, etc. laminated. Here, a charge transport layer such as a hole transport layer or an electron transport layer, does not emit light by itself, but plays roles to facilitate charge injection to the luminescent layer and to confine the charge injected to the luminescent layer and the energy of excitons formed in the luminescent layer. Thus, the charge transport layer bears very important roles to reduce the driving voltage and to improve the luminous efficiency of an organic EL device.

As the material for a hole transport layer, an amine having a proper ionization potential and hole transporting ability is employed, and for example, 4,4'-bis[N-(1-naphthyl)-N-phenylamino]biphenyl (hereinafter abbreviated as NPD) is well known. However, the driving voltage, luminous efficiency and durability of the device employing NPD as the material for a hole transport layer, are not sufficiently good, and it is desired to develop a new material. Further, in recent years, development of an organic EL device employing a phosphorescent emitting material for a luminescent layer has been in progress, and in the device employing phosphorescent, a material for a hole transport layer having a high triplet level is required. Also from the viewpoint of the triplet level, NPD is not adequate, and for example, it has been reported that the luminous efficiency decreases in an organic EL device wherein a green-emitting phosphorescent emitting material and NPD are combined (see e.g. Non-patent Document 1).

Under such circumstances, recently, there have been reports on an amine compound having a carbazole ring introduced to its molecule, as a material for a hole transport layer. Specifically, reports on a 2-aminocarbazole compound may be mentioned (see e.g. Patent Documents 1 and 2). The 2-aminocarbazole compound has an ionization potential equal to or higher than NPD and a triplet level higher than NPD. Therefore, it is known that the 2-aminocarbazole compound usually tends to exhibit higher luminous efficiency than NPD in a device employing a green phosphorescent material.

Further, a 3-aminocabazole compound having carbazole combined with dibenzothiophene or dibenzofuran, has also been disclosed (see e.g. Patent Document 3).

However, with respect to an organic EL device, further reduction of the driving voltage, higher luminous efficiency and longer lifetime are desired, and it is desired to develop a material for a hole transport layer for such purposes.

PRIOR ART DOCUMENTS

Patent Documents

Patent Document 1: KR 10-2009-0129799
Patent Document 2: JP-A-2011-001349
Patent Document 3: WO2011/122132

Non-Patent Document

Non-patent Document 1: Journal of Applied Physics, 2004, Vol. 95, p. 7798

DISCLOSURE OF INVENTION

Technical Problem

It is an object of the present invention to provide a novel 2-aminocarbazole compound which is capable of distinctly improving the lifetime of an organic EL device as compared with known 2-aminocarbazole compounds, and to provide an organic EL device which employs such a novel 2-aminocarbazole compound and which is excellent in the long lifetime.

Solution to Problem

As a result of an extensive study, the present inventors have found a novel amine compound represented by the following formula (1) and having a 2-benzofuranyl group or a 2-benzothienyl group at the 9-position of carbazole ring, and have accomplished the present invention by utilizing such a novel amine compound.

The present invention provides the following as its gist.
(1) An amine compound characterized in that it is represented by the formula (1):

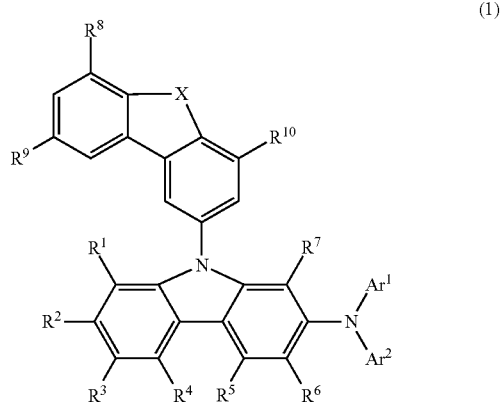

(1)

(wherein X is a sulfur atom or an oxygen atom, each of $R^1$ to $R^{10}$ which are independent of one another, is a hydrogen atom, a deuterium atom or a phenyl group, and each of $Ar^1$ and $Ar^2$ which are independent of each other, is a $C_{6-18}$ aromatic hydrocarbon group, a dibenzothienyl group or a dibenzofuranyl group, which, each independently, may have a substituent consisting of a methyl group, a methoxy group, a dibenzothienyl group, a dibenzofuranyl group or a 9-carbazolyl group.).
(2) The amine compound according to the above (1), wherein $R^1$, $R^2$, $R^4$, $R^5$, $R^7$, $R^8$, $R^9$ and $R^{10}$ are hydrogen atoms.
(3) The amine compound according to the above (1) or (2), wherein $R^1$ to $R^{10}$ are hydrogen atoms.
(4) The amine compound according to any one of the above (1) to (3), wherein each of $Ar^1$ and $Ar^2$ which are independent of each other, is
a phenyl group which may have a substituent selected from the group consisting of a methyl group, a methoxy group, a dibenzothienyl group, a dibenzofuranyl group and a 9-carbazolyl group, a biphenylyl group which may have a substituent consisting of a methyl group or a methoxy group, a terphenyl group which may have a substituent consisting of a methyl group or a methoxy group, a 9,9-dimethyl-9H-fluorenyl group which may have a substituent consisting of a methyl group or a methoxy group, a dibenzothienyl group which may have a substituent consisting of a methyl group or a methoxy group, or a dibenzofuranyl group which may have a substituent consisting of a methyl group or a methoxy group.

(5) The amine compound according to any one of the above (1) to (4), wherein each of Ar¹ and Ar² which are independent of each other, is a phenyl group, a p-tolyl group, a p-methoxyphenyl group, a 4-biphenylyl group, a p-terphenyl-4-yl group, a m-terphenyl-4-yl group, a 9,9-dimethylfluoren-2-yl group, a dibenzothiophen-2-yl group, a dibenzofuran-2-yl group, a 4-(dibenzothiophen-2-yl)phenyl group, a 4-(dibenzothiophen-4-yl)phenyl group, a 4-(dibenzofuran-2-yl)phenyl group or a 4-(9-carbazolyl)phenyl group.

(6) The amine compound according to any one of the above (1) to (5), wherein X is a sulfur atom.

(7) The amine compound according to any one of the above (1) to (5), which is represented by one of the following formulae:

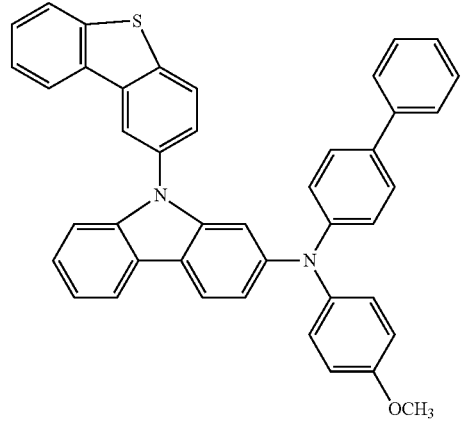

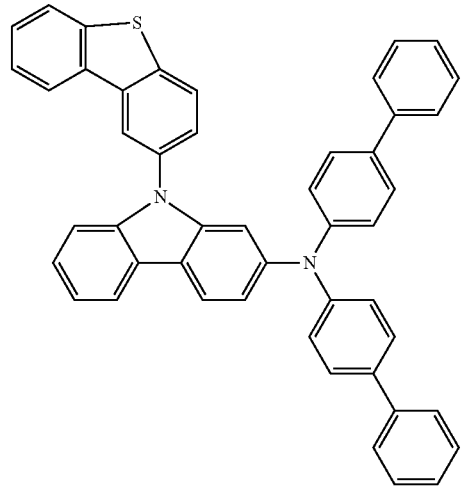

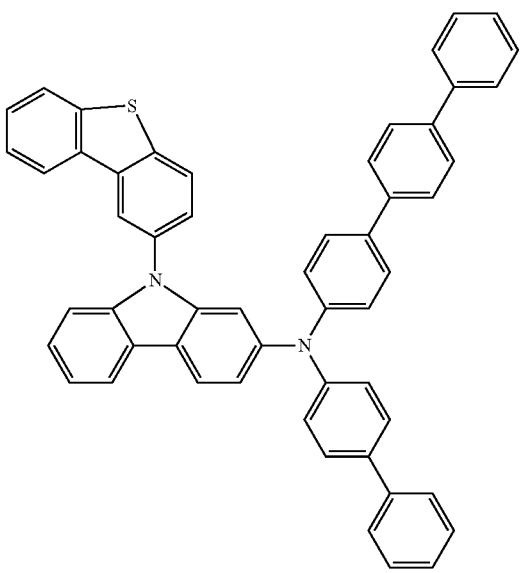

(A13)
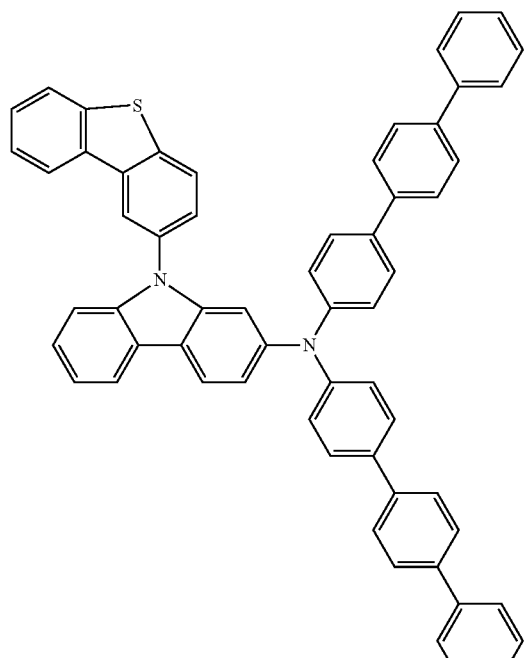
(A16)
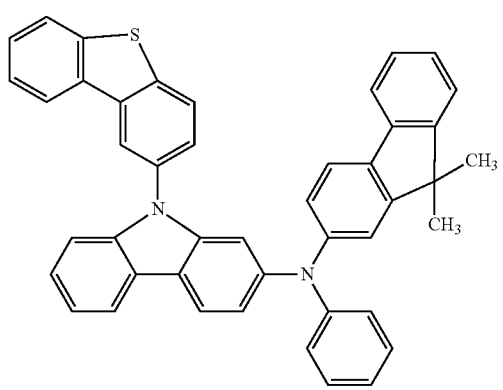
(A22)
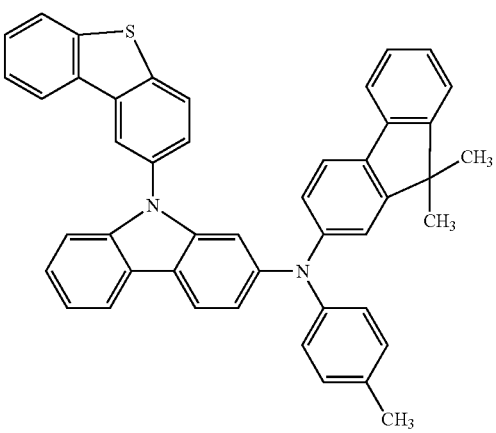
(A24)
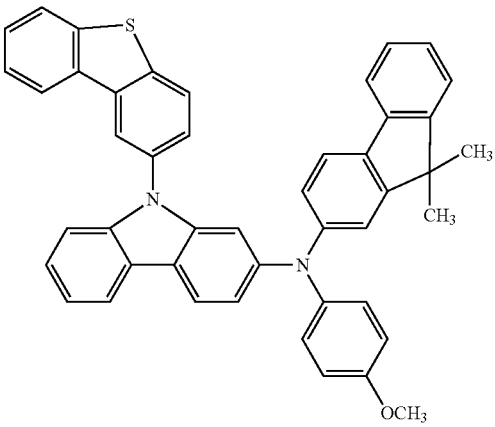
(A25)
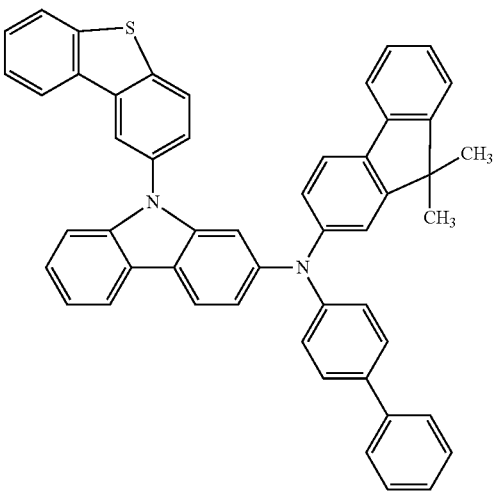
(A21)

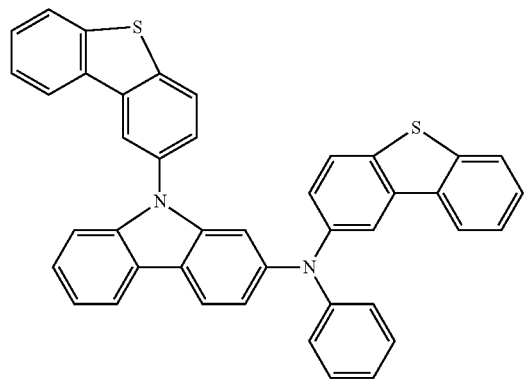
(A28)
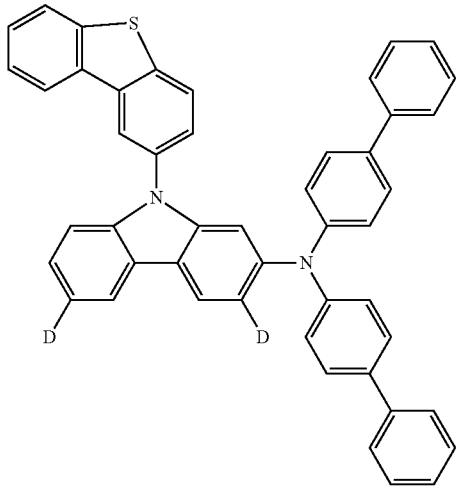
(A46)
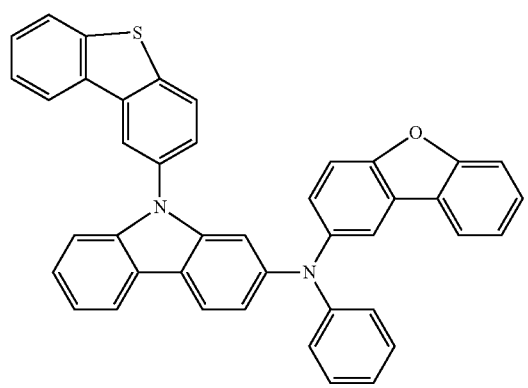
(A32)
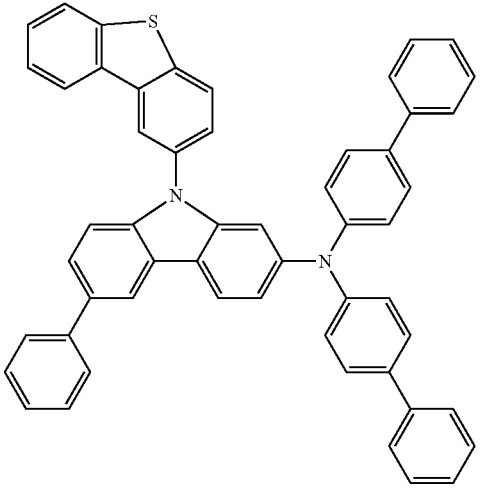
(A47)
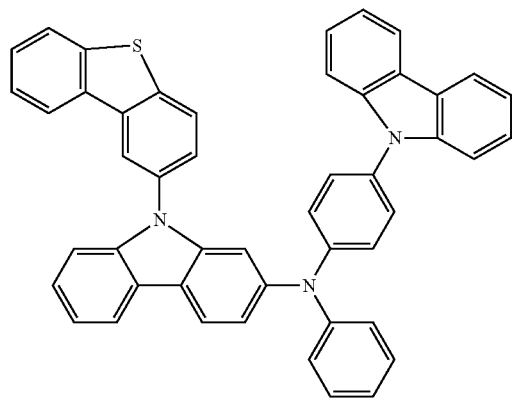
(A36)
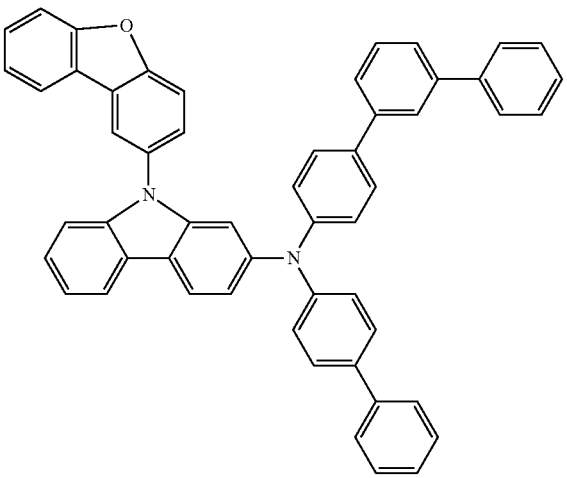
(B4)

-continued

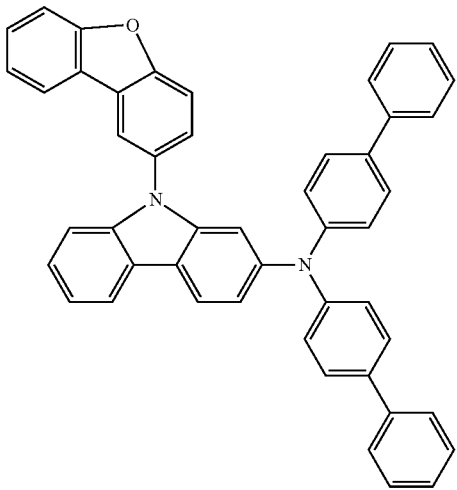

(B8)

(8) A hole transport layer containing the amine compound as defined in any one of the above (1) to (7).
(9) A hole injection layer containing the amine compound as defined in any one of the above (1) to (7).
(10) A luminescent layer containing the amine compound as defined in any one of the above (1) to (7).
(11) An organic EL device containing the amine compound as defined in any one of the above (1) to (7) in at least one of a luminescent layer, a hole transport layer and a hole injection layer.
(12) The organic EL device according to the above (11), which contains the amine compound as defined in any one of the above (1) to (7) in a hole transport layer.

Advantageous Effects of Invention

The organic EL device employing the amine compound of the present invention is distinctly excellent in the device lifetime as compared with organic EL devices employing known 2-aminocarbazole compounds. Further, as compared also with NPD being a known hole transport material, it is possible to prolong the lifetime, to reduce the driving voltage and to increase the luminous efficiency of an organic EL device. Therefore, the amine compound of the present invention is useful as an organic EL material excellent in durability.

Thus, according to the present invention, it is possible to provide an organic EL device whereby power consumption is low and which is excellent in the device lifetime.

DESCRIPTION OF EMBODIMENTS

In the amine compound represented by the above formula (1), X is an oxygen atom or a sulfur atom. Here, from the viewpoint of hole transporting properties, X is preferably a sulfur atom.

In the amine compound represented by the above formula (1), each of $R^1$ to $R^{10}$ which are independent of one another, is a hydrogen atom, a deuterium atom or a phenyl group. Here, from the viewpoint of the triplet level, the hole transporting properties and availability of raw material, $R^1$, $R^2$, $R^4$, $R^5$, $R^7$, $R^8$, $R^9$ and $R^{10}$ are preferably hydrogen atoms. Further, $R^1$ to $R^{10}$ are particularly preferably hydrogen atoms from the viewpoint of the triplet level, the hole transporting properties and availability of raw material.

In the amine compound represented by the above formula (1), each of $Ar^1$ and $Ar^2$ which are independent of each other, is a $C_{6-18}$ aromatic hydrocarbon group, a dibenzothienyl group or a dibenzofuranyl group, which, each independently, may have a methyl group, a methoxy group, a dibenzothienyl group, a dibenzofuranyl group or a 9-carbazolyl group.

The $C_{6-18}$ aromatic hydrocarbon group in $Ar^1$ and $Ar^2$ is not particularly limited, but may, for example, be a phenyl group, a biphenylyl group, a terphenylyl group, a naphthyl group, a fluorenyl group, a phenanthryl group or a benzofluorenyl group (which, each independently, may have a methyl group, a methoxy group, a dibenzothienyl group, a dibenzofuranyl group or a 9-carbazolyl group, and the number of such substituents is not particularly limited). Among them, a phenyl group which may have a substituent selected from the group consisting of a methyl group, a methoxy group, a dibenzothienyl group, a dibenzofuranyl group and a 9-carbazolyl group, a biphenylyl group which may have a methyl group or a methoxy group, a terphenyl group which may have a methyl group or a methoxy group, or a 9,9-dimethyl-9-H-fluorenyl group which may have a methyl group or a methoxy group, is preferred, from the viewpoint of excellent hole transporting properties.

With respect to a dibenzothienyl group or a dibenzofuranyl group in $Ar^1$ and $Ar^2$, its linkage position is not particularly limited, but is preferably the 2-position of the dibenzothienyl group or the dibenzofuranyl group. Further, each of the dibenzothienyl group and the dibenzofuranyl group which are independent of each other, may have a methyl group, a methoxy group, a dibenzothienyl group, a dibenzofuranyl group or a 9-carbazolyl group, however, the position of such a substituent and the number of such substituents to be bonded, are not particularly limited.

As specific examples of $Ar^1$ and $Ar^2$, a phenyl group, a 4-methylphenyl group, a 3-methylphenyl group, a 2-methylphenyl group, a 2,4-dimethylphenyl group, a 2,5-dimethylphenyl group, a 3,4-dimethylphenyl group, a 3,5-dimethylphenyl group, a 2,6-dimethylphenyl group, a 2,3,5-trimethylphenyl group, a 2,3,6-trimethylphenyl group, a 3,4,5-trimethylphenyl group, a 4-methoxyphenyl group, a 3-methoxyphenyl group, a 2-methoxyphenyl group, a 2-methyl-4-methoxyphenyl group, a 2-methyl-5-methoxyphenyl group, a 3-methyl-4-methoxyphenyl group, a 3-methyl-5-methoxyphenyl group, a 2-methoxy-4-methylphenyl group, a 3-methoxy-4-methylphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 3,4,5-trimethoxyphenyl group, a 4-biphenylyl group, a 3-biphenylyl group, a 2-biphenylyl group, a 2-methyl-1,1'-biphenyl-4-yl group, a 3-methyl-1,1'-biphenyl-4-yl group, a 2'-methyl-1,1'-biphenyl-4-yl group, a 3'-methyl-1,1'-biphenyl-4-yl group, a 4'-methyl-1,1'-biphenyl-4-yl group, a 2,6-dimethyl-1,1'-biphenyl-4-yl group, a 2,2'-dimethyl-1,1'-biphenyl-4-yl group, a 2,3'-dimethyl-1,1'-biphenyl-4-yl group, a 2,4'-dimethyl-1,1'-biphenyl-4-yl group, a 3,2'-dimethyl-1,1'-biphenyl-4-yl group, a 2',3'-dimethyl-1,1'-biphenyl-4-yl group, a 2',4'-dimethyl-1,1'-biphenyl-4-yl group, a 2',5'-dimethyl-1,1'-biphenyl-4-yl group, a 2',6'-dimethyl-1,1'-biphenyl-4-yl group, a p-terphenyl group, a m-terphenyl group, an o-terphenyl group, a 1-naphthyl group, a 2-naphthyl group, a 2-methylnaphthalen-1-yl group, a 4-methylnaphthalen-1-yl group, a 6-methylnaphthalen-2-yl group, a 2-anthryl group, a 9-anthryl group, a 2-fluorenyl group, a 9,9-dimethyl-2-fluorenyl group, a 9-phenanthryl group, a 2-phenanthryl group, a benzofluorenyl group, a fluoranthenyl group, a pyrenyl group, a chrysenyl group, a 2-dibenzothienyl group, a 3-dibenzothienyl group, a 4-dibenzothienyl group, a 2-dibenzofuranyl group, a 3-dibenzofuranyl group, a 4-dibenzofuranyl group, a 4-(dibenzothiophen-2-yl)phenyl group, a 4-(dibenzothiophen-4-yl)phenyl group, a 3-(dibenzothiophen-2-yl)phenyl group, a 3-(dibenzothiophen-4-yl) phenyl group, a 4-(dibenzofuran-2-yl)phenyl group, a 4-(dibenzofuran-4-yl)phenyl group, a 3-(dibenzofuran-2-yl) phenyl group, a 3-(dibenzofuran-4-yl)phenyl group, a 4-(9-carbazolyl)phenyl group, a 3-(9-carbazolyl)phenyl group, etc. may be exemplified, although not limited thereto.

From the viewpoint of the triplet level and the hole transporting properties, each of $Ar^1$ and $Ar^2$ in the amine compound represented by the formula (1), which are independent of each other, is preferably a phenyl group which may have a substituent selected from the group consisting of a methyl group, a methoxy group, a dibenzothienyl group, a dibenzofuranyl group and a 9-carbazolyl group, a biphenylyl group which may have a methyl group or a methoxy group, a terphenyl group which may have a methyl group or a methoxy group, a 9,9-dimethyl-9H-fluorenyl group which may have a methyl group or a methoxy group, a dibenzothienyl group which may have a methyl group or a methoxy group, or a dibenzofuranyl group which may have a methyl group or a methoxy group. Specifically, each independently may be a phenyl group, a p-tolyl group, a p-methoxyphenyl group, a 4-biphenylyl group, a p-terphenyl-4-yl group, a m-terphenyl-4-yl group, a 9,9-dimethylfluoren-2-yl group, a dibenzothiophen-2-yl group, a dibenzofuran-2-yl group, a 4-(dibenzothiophen-2-yl)phenyl group, a 4-(dibenzothiophen-4-yl)phenyl group, a 4-(dibenzofuran-2-yl)phenyl group or a 4-(9-carbazolyl)phenyl group.

Each of $Ar^1$ and $Ar^2$ in the amine compound represented by the formula (1), which are independent of each other, is more preferably a phenyl group which may have a substituent selected from the group consisting of a methyl group, a methoxy group and a 9-carbazolyl group, a biphenylyl group which may have a methyl group or a methoxy group, a terphenyl group which may have a methyl group or a methoxy group, or a 9,9-dimethyl-9H-fluorenyl group which may have a methyl group or a methoxy group. Specifically, each independently may be a phenyl group, a p-tolyl group, a p-methoxyphenyl group, a 4-biphenylyl group, a p-terphenyl-4-yl group, a m-terphenyl-4-yl group, a 9,9-dimethylfluoren-2-yl group or a 4-(9-carbazolyl)phenyl group.

Now, with respect to the amine compound represented by the formula (1), preferred compounds will be exemplified, but preferred ones are not limited to these compounds.

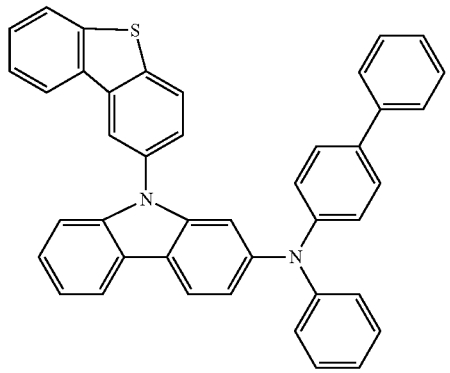

(A1)

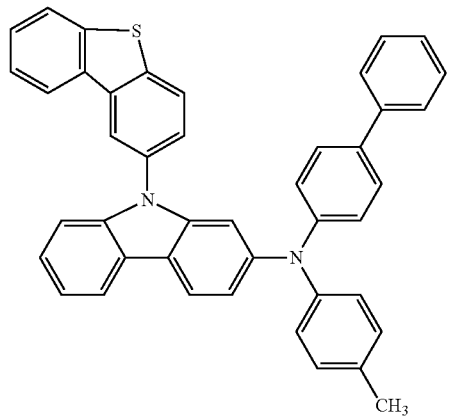

(A2)

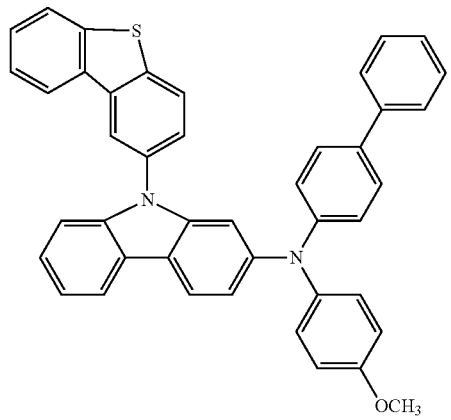

(A3)

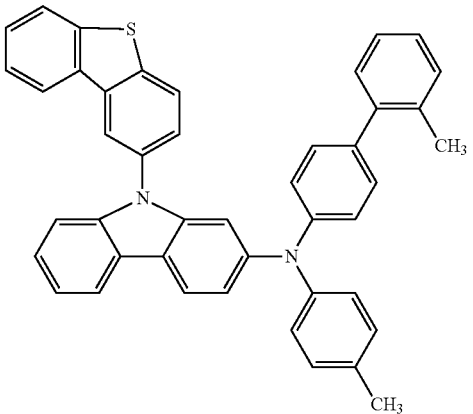

(A4)

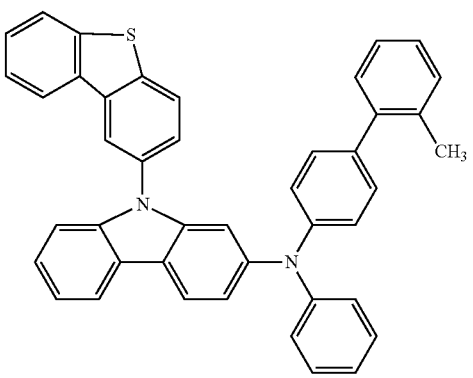

(A5)

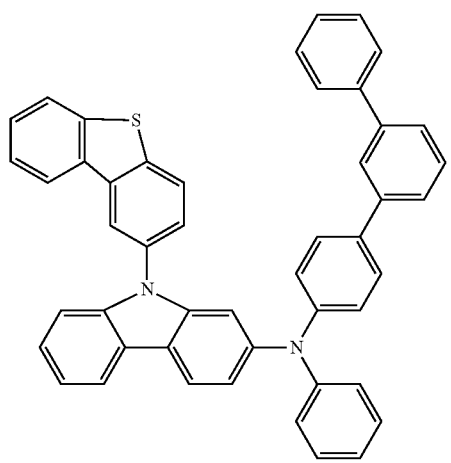
(A6)
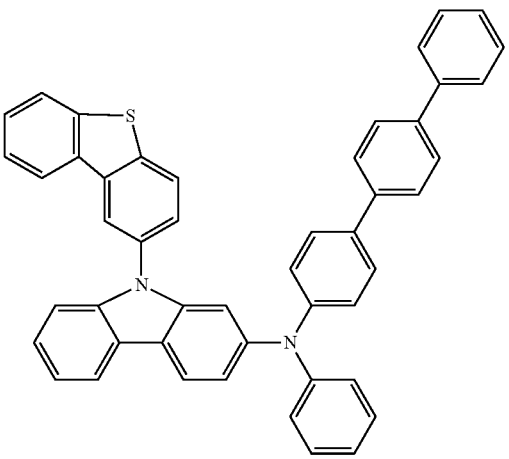
(A9)
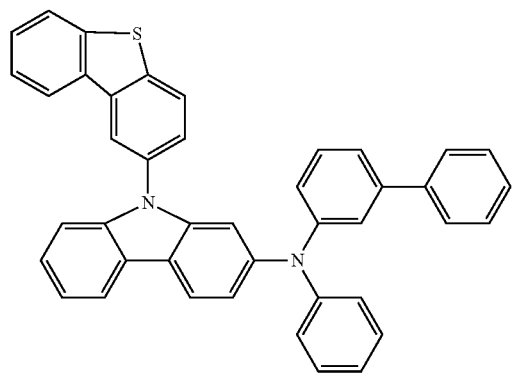
(A7)
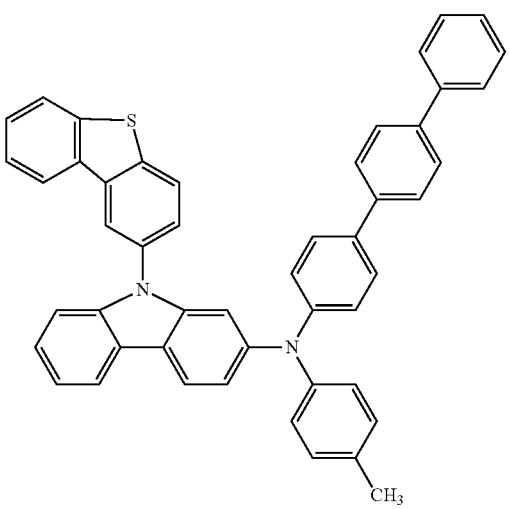
(A10)
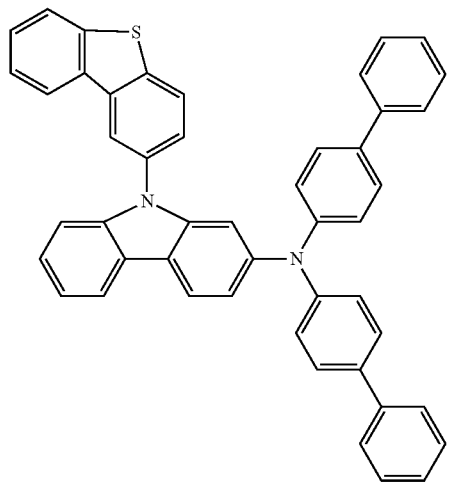
(A8)
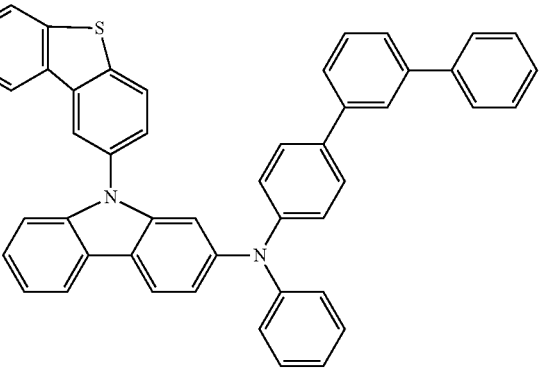
(A11)

(A12)
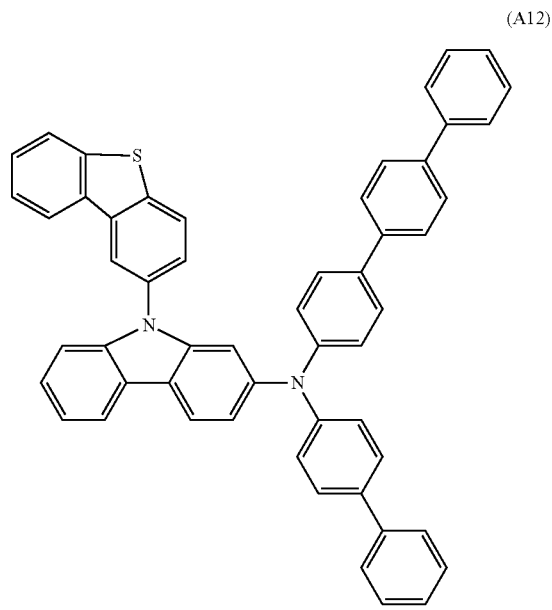
(A13)
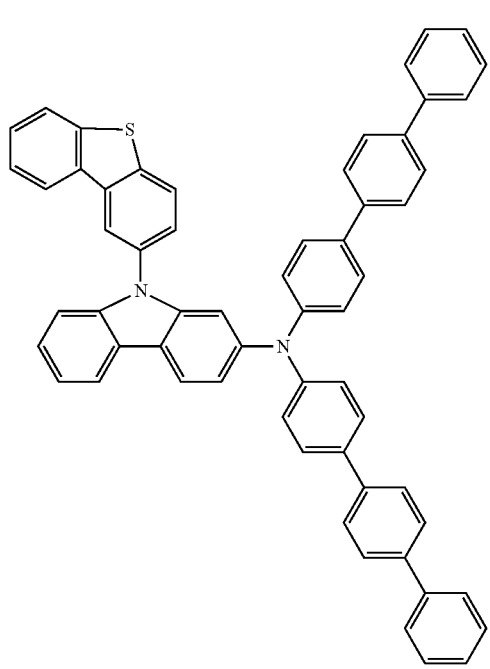
(A14)
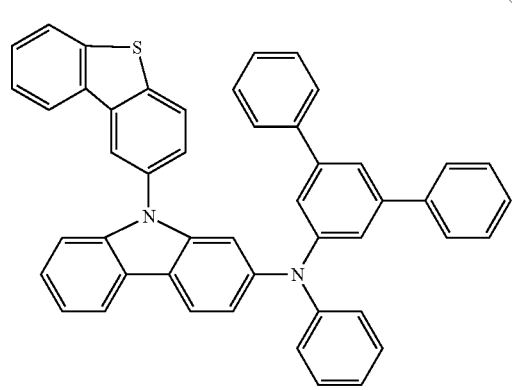
(A15)
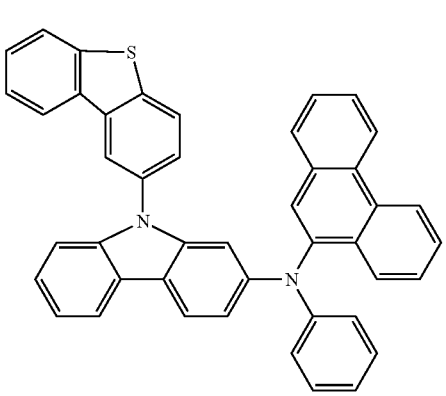
(A16)
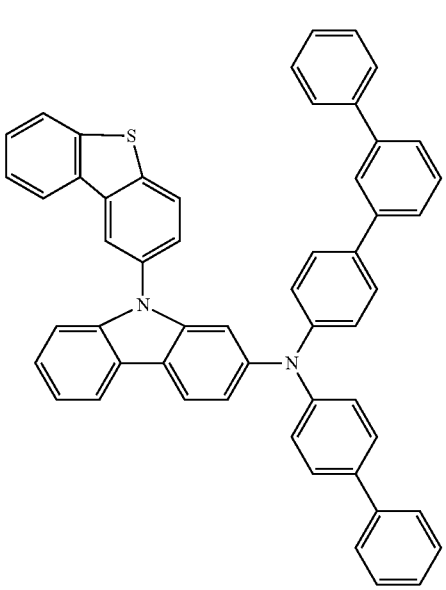
(A17)
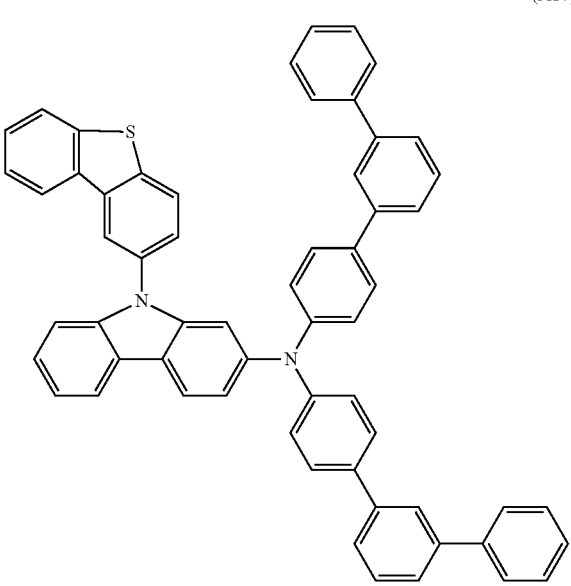

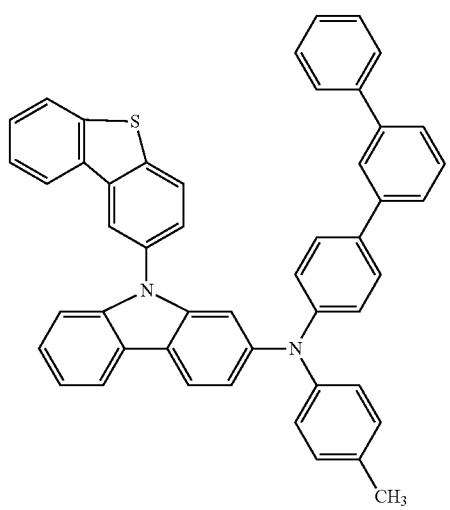
(A18)
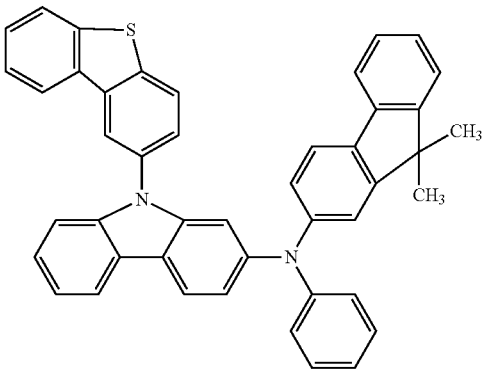
(A21)
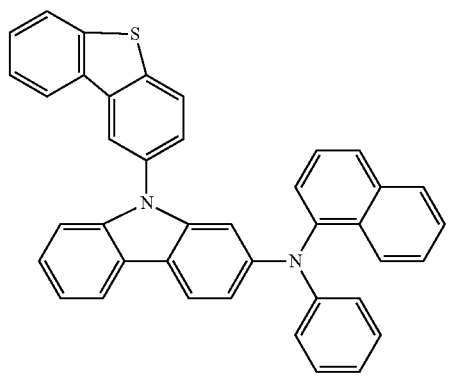
(A19)
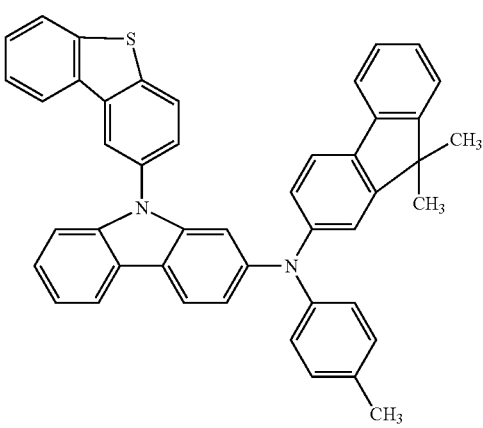
(A22)
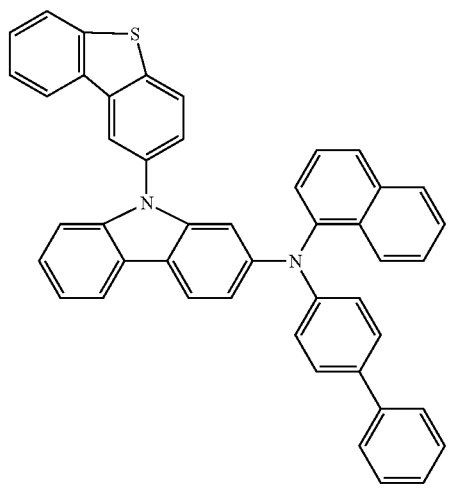
(A20)
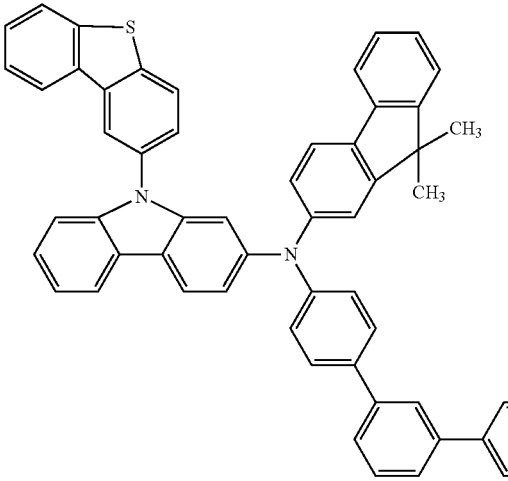
(A23)

(A24)
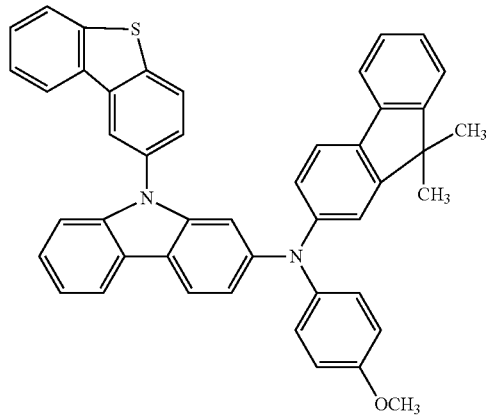
(A25)
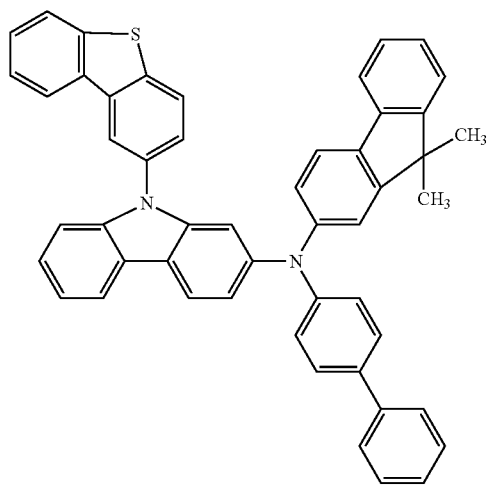
(A26)
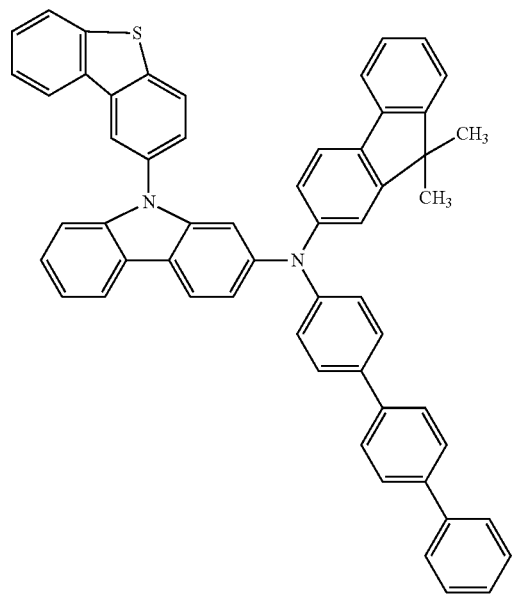
(A27)
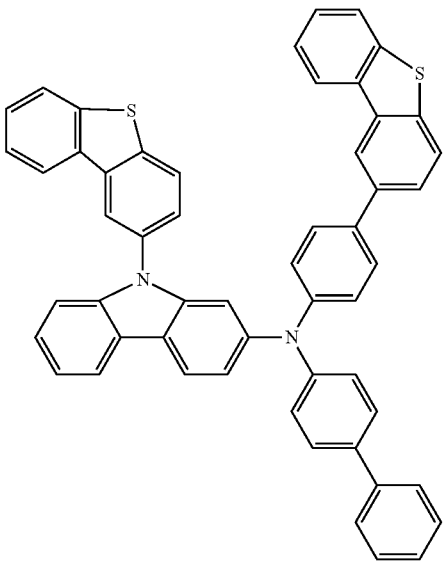
(A28)
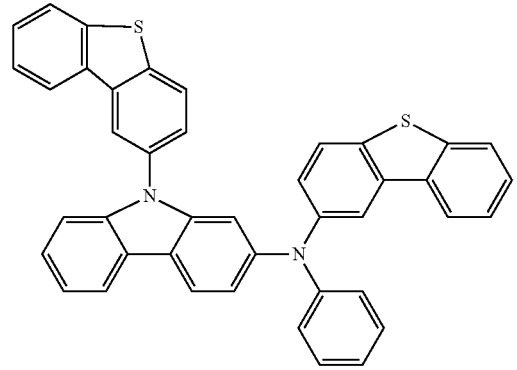
(A29)
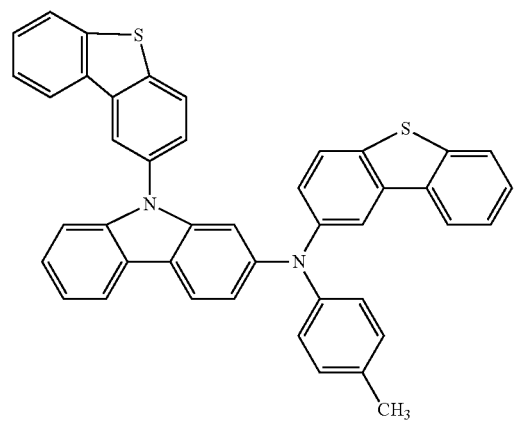

(A30)
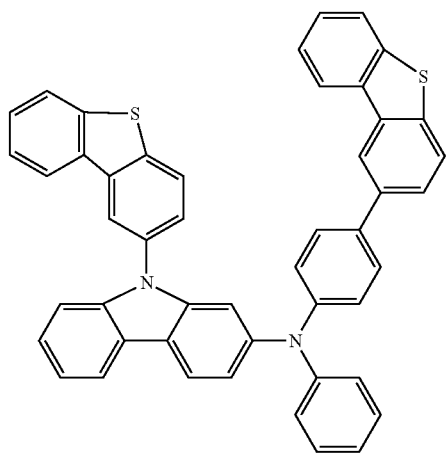
(A31)
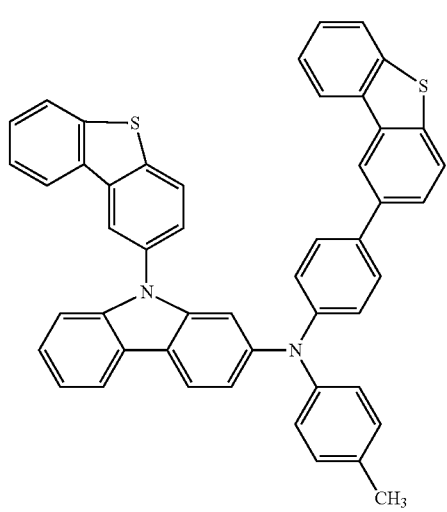
(A32)
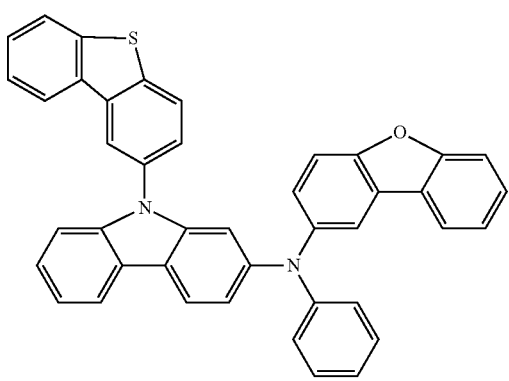
(A33)
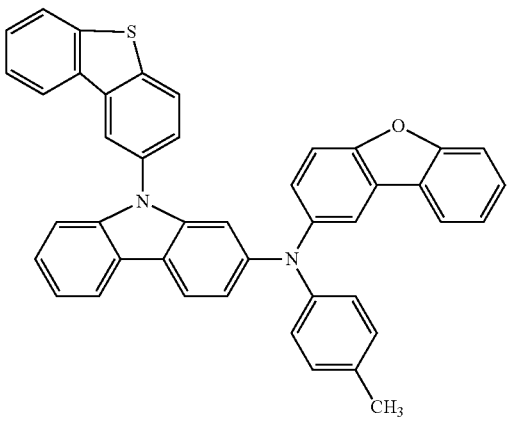
(A34)
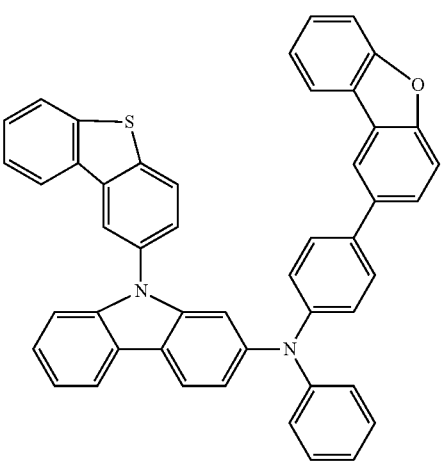
(A35)
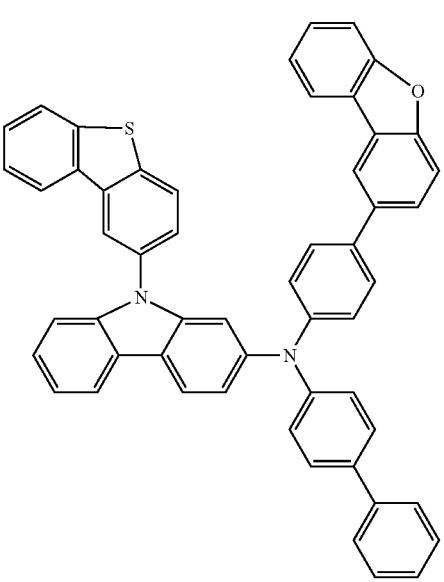

(A36)
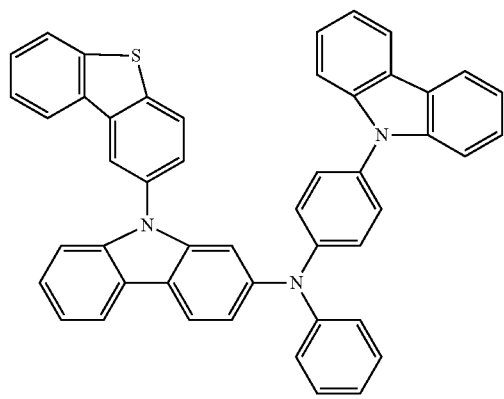
(A39)
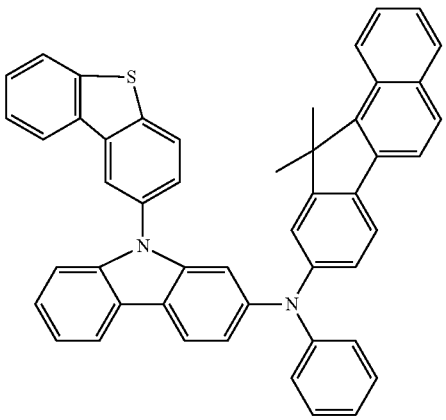
(A37)
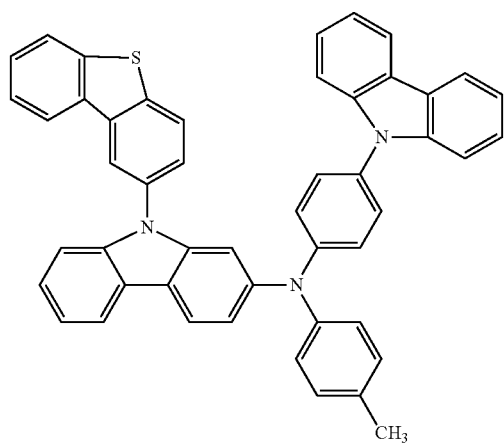
(A40)
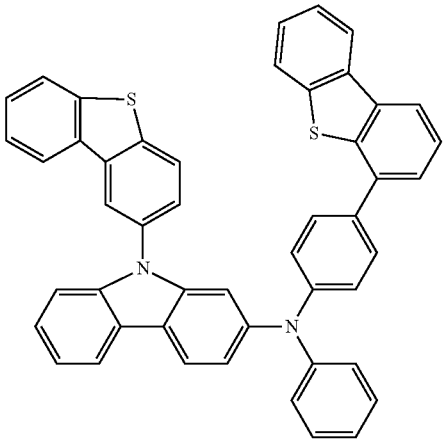
(A38)
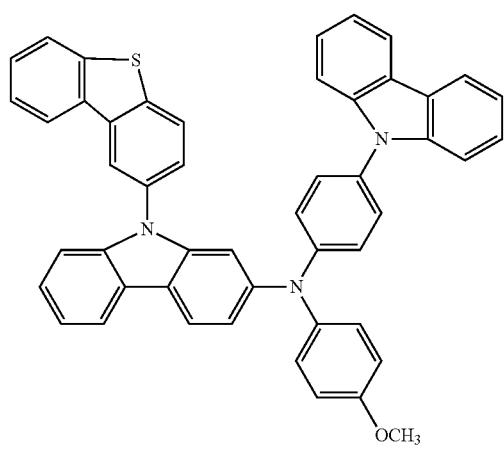
(A41)
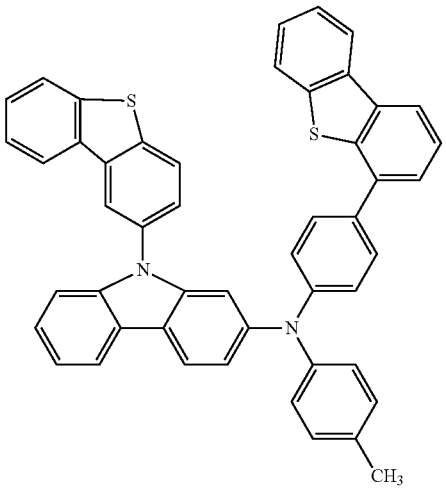

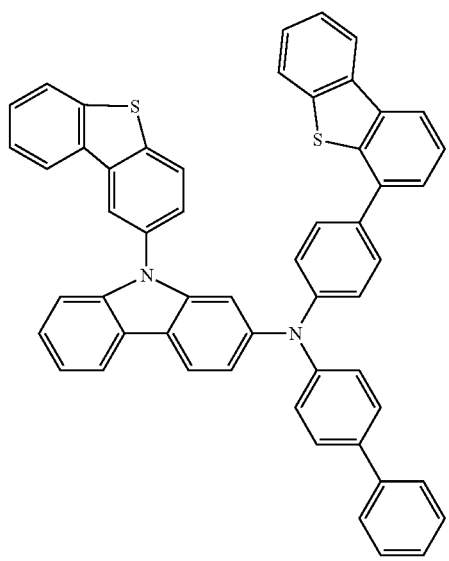
(A42)
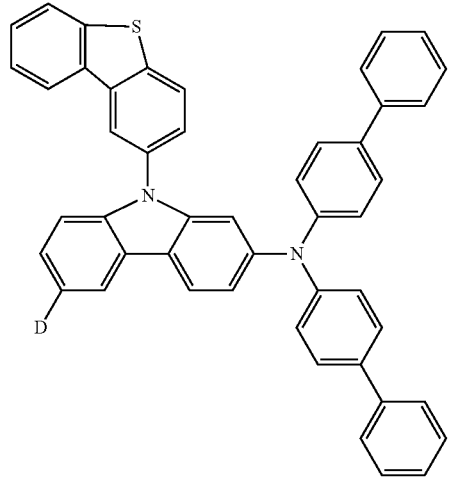
(A45)
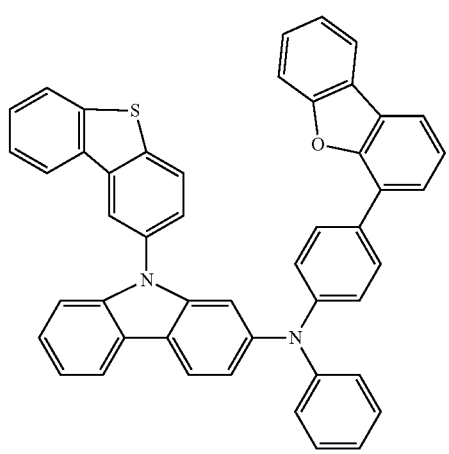
(A43)
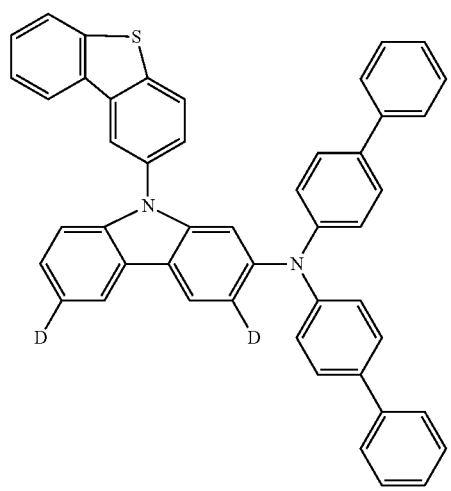
(A46)
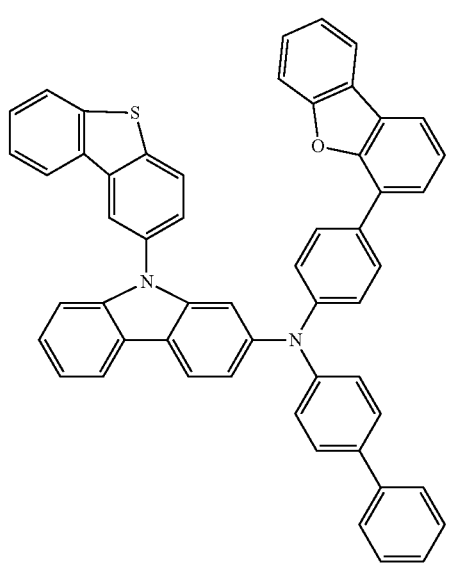
(A44)
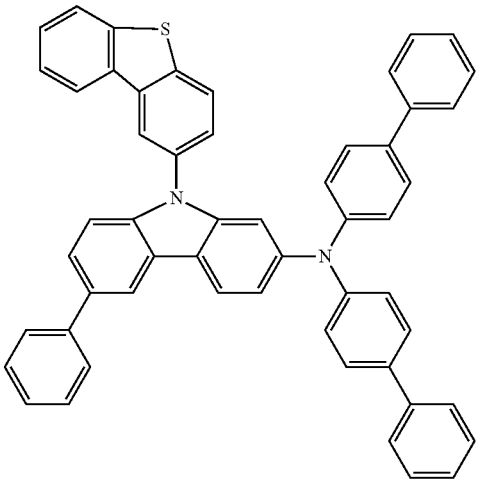
(A47)

-continued
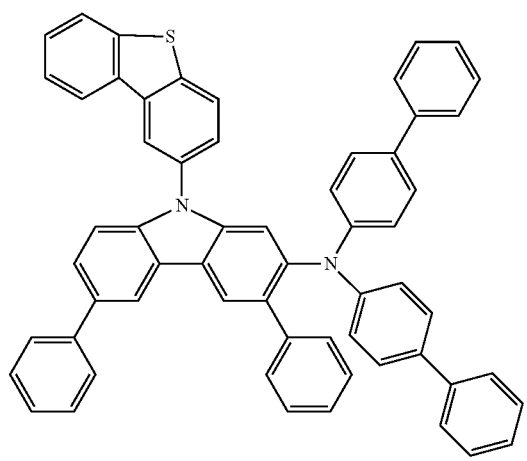
(A48)
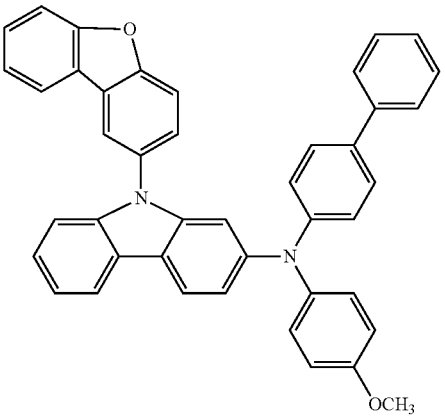
(B3)
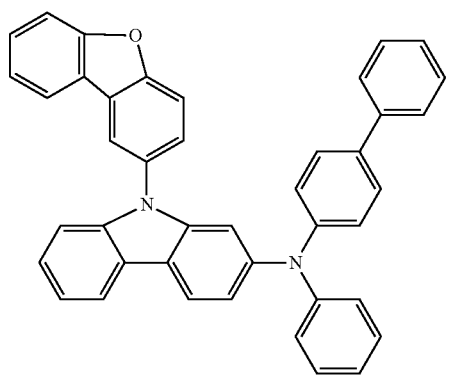
(B1)
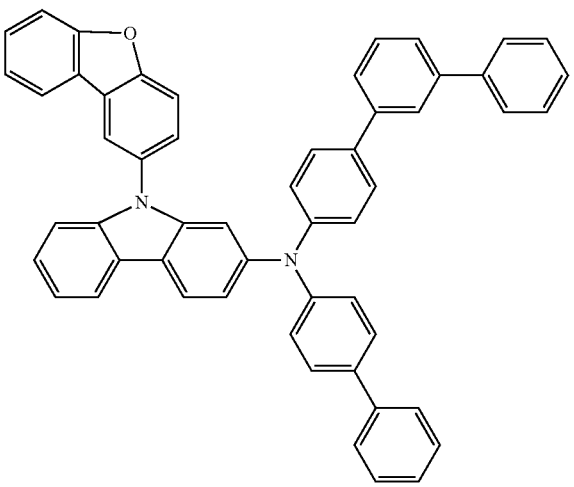
(B4)
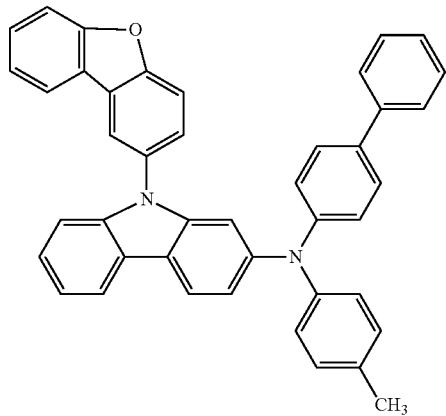
(B2)
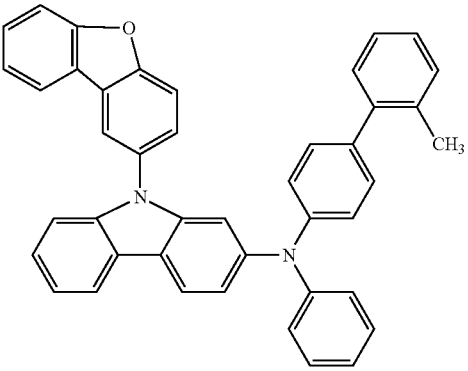
(B5)

(B6)
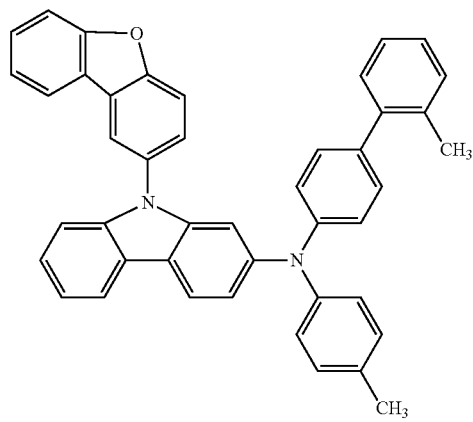
(B7)
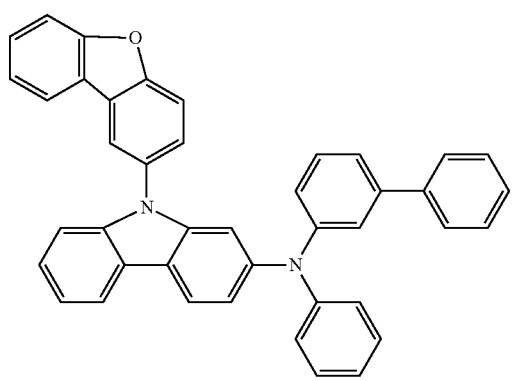
(B8)
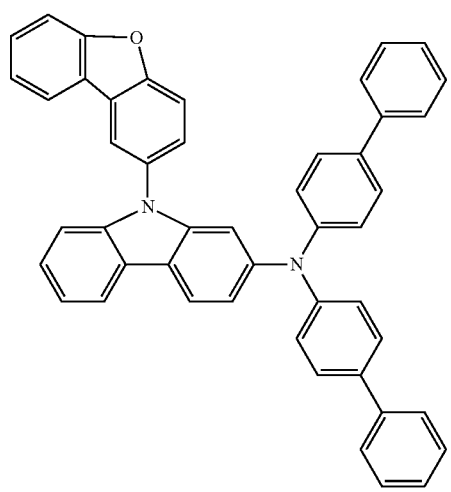
(B9)
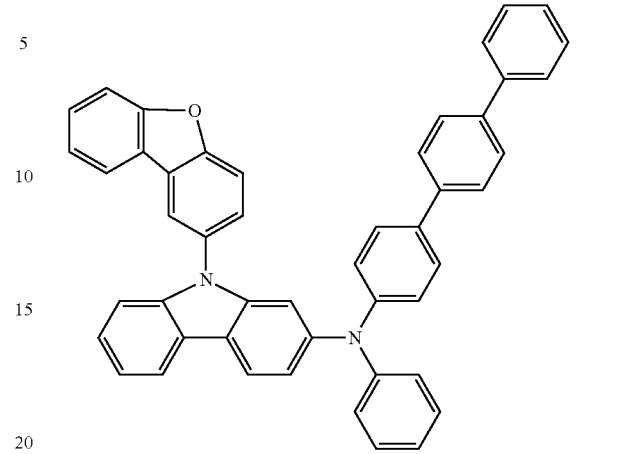
(B10)
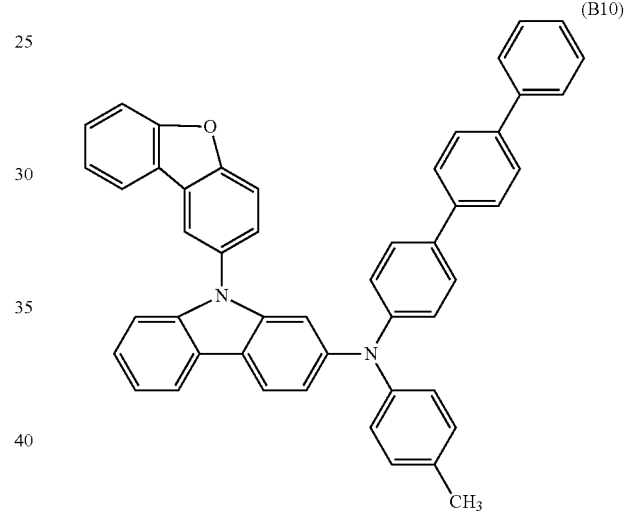
(B11)
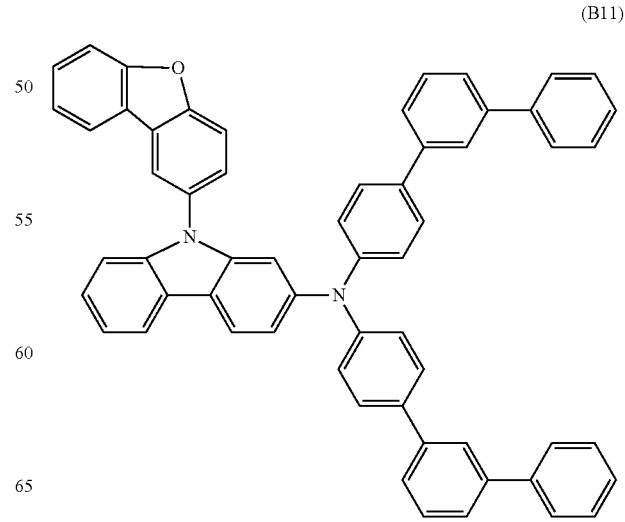

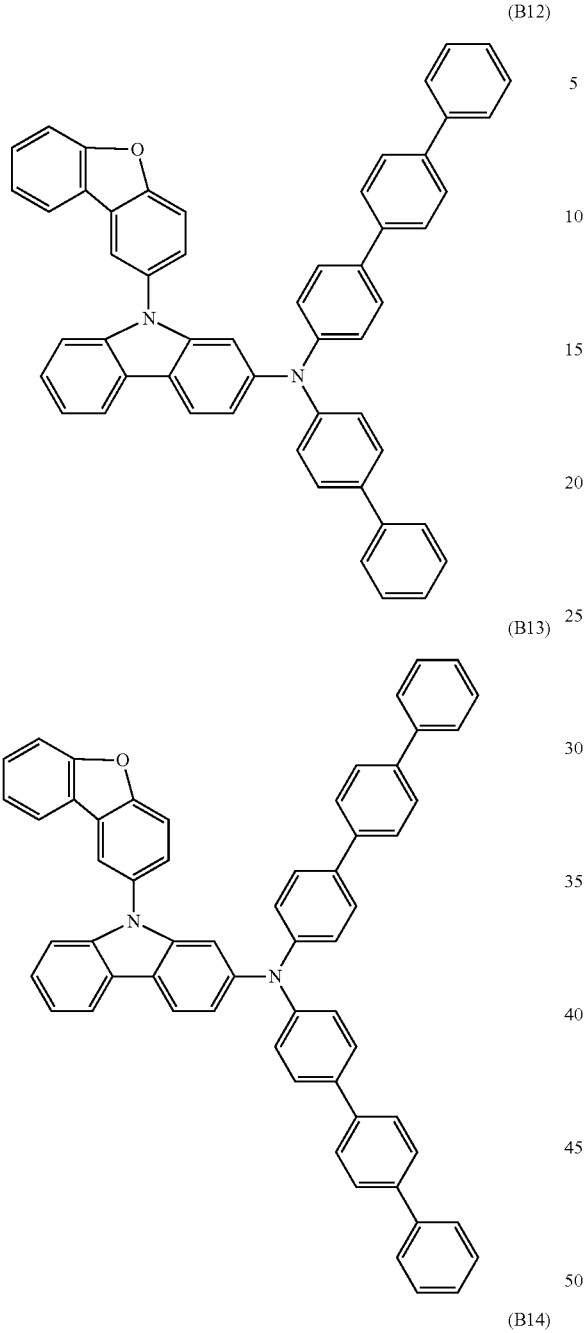
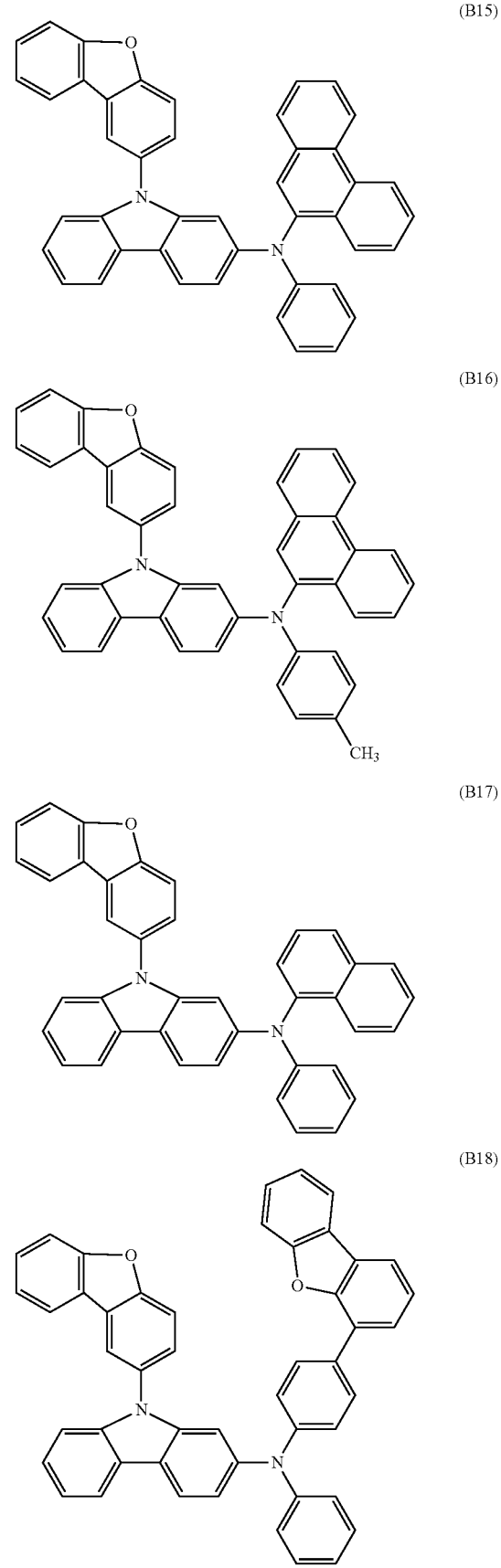

(B19)
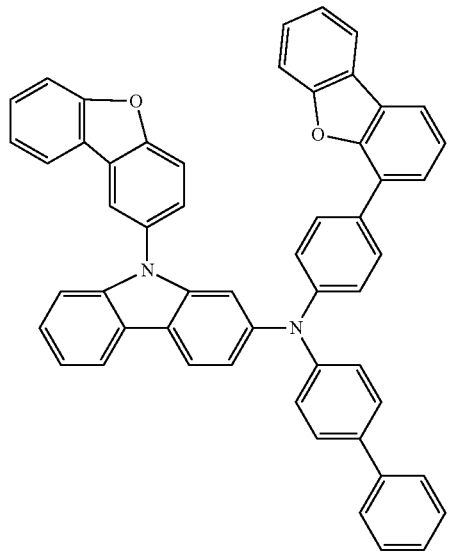
(B20)
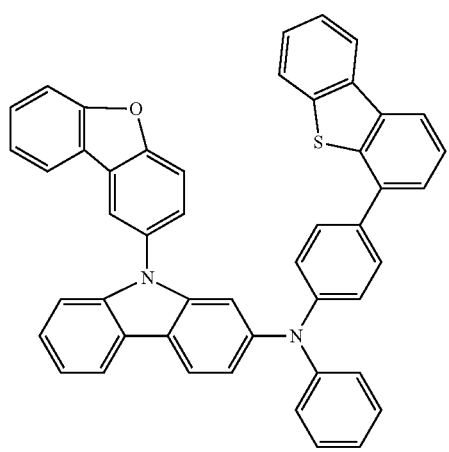
(B21)
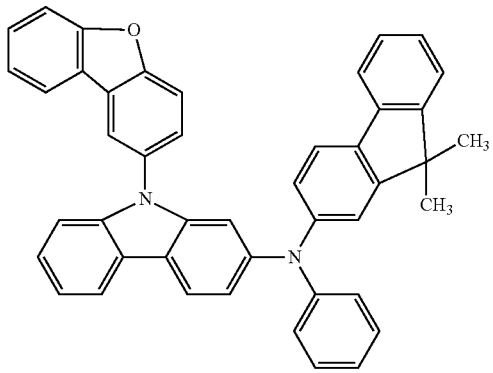
(B22)
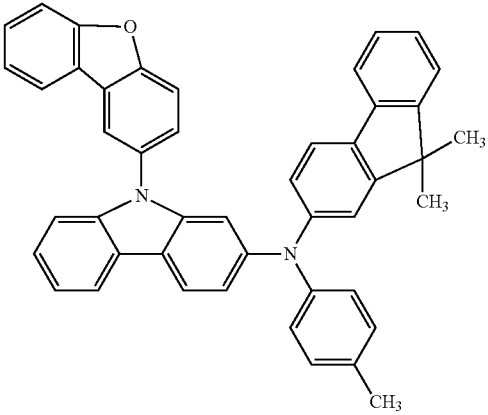
(B23)
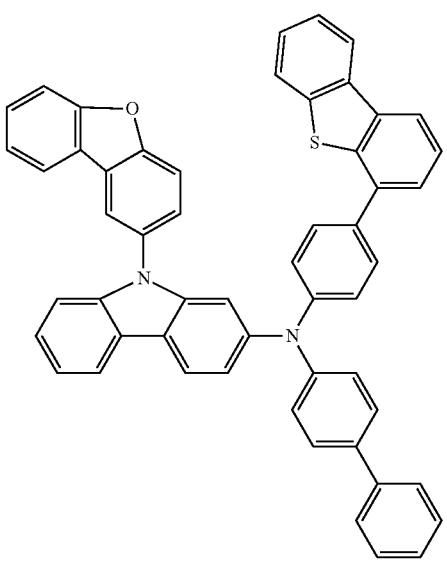
(B24)
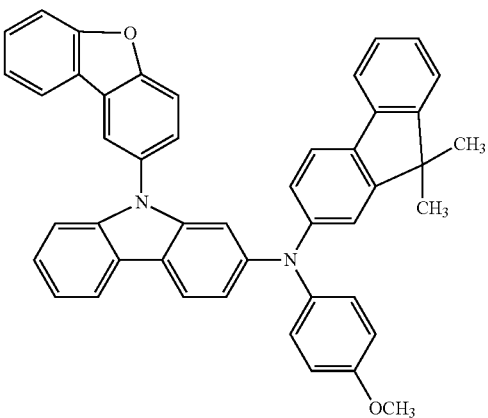

(B25)
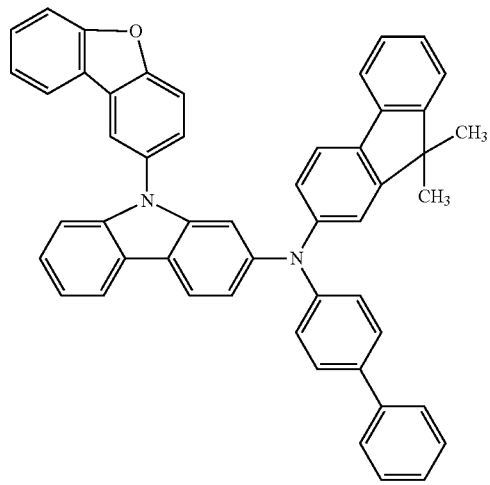
(B26)
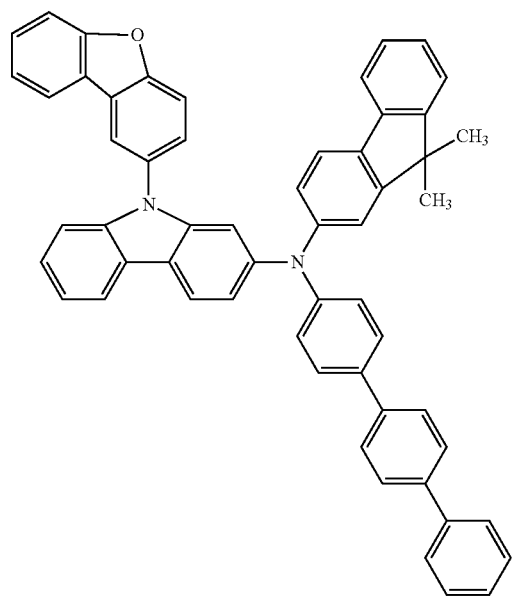
(B27)
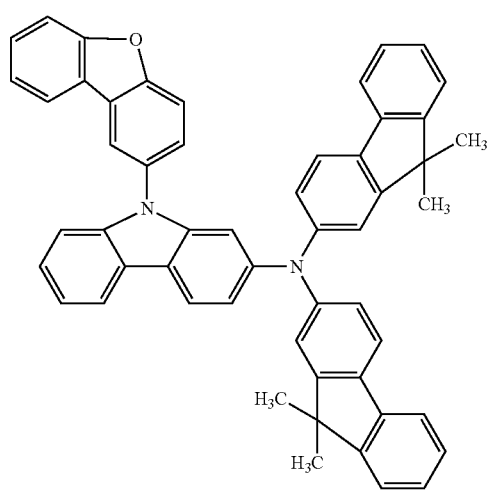
(B28)
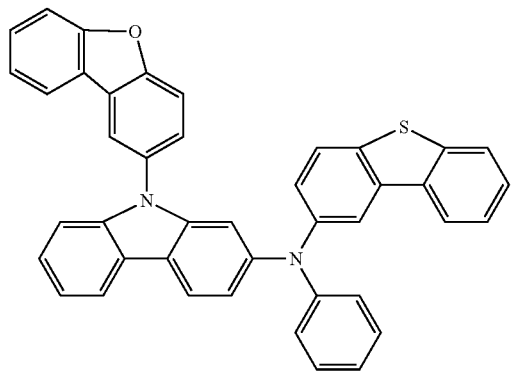
(B29)
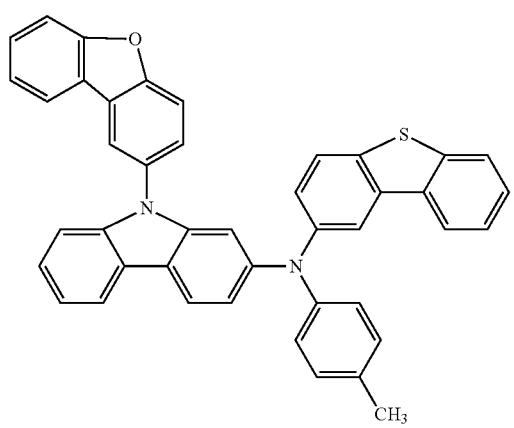
(B30)
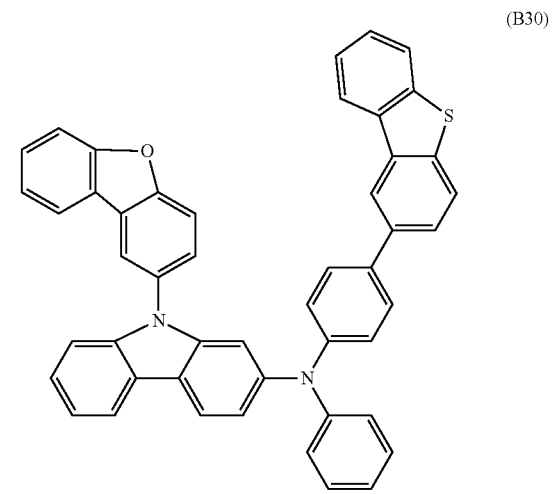

(B31)
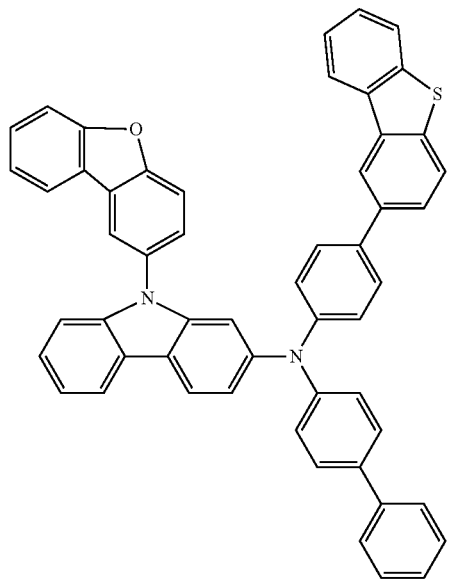
(B32)
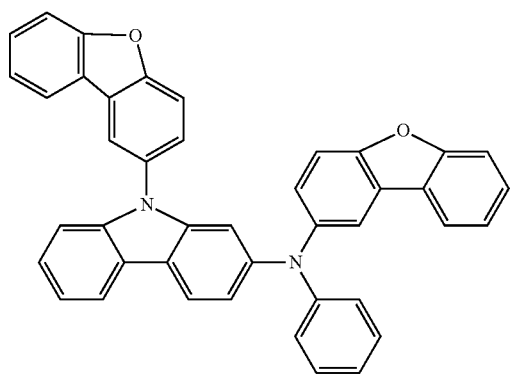
(B33)
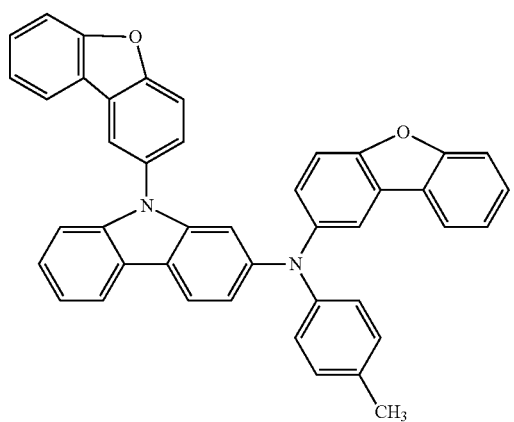
(B34)
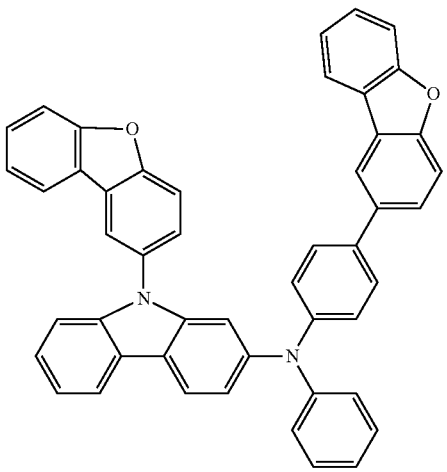
(B35)
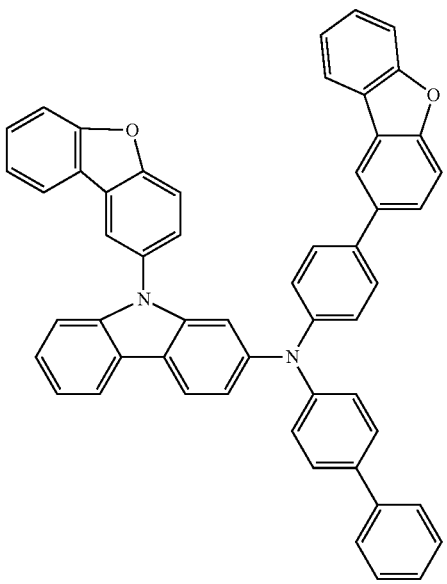
(B36)
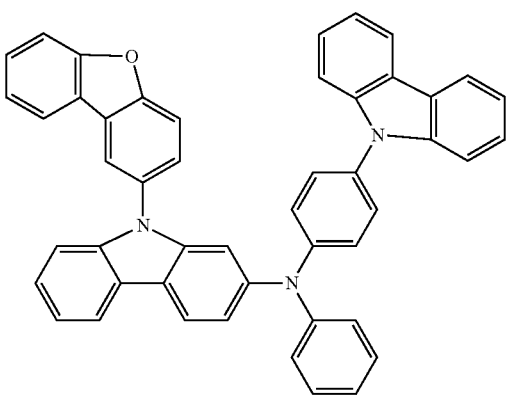

(B37)
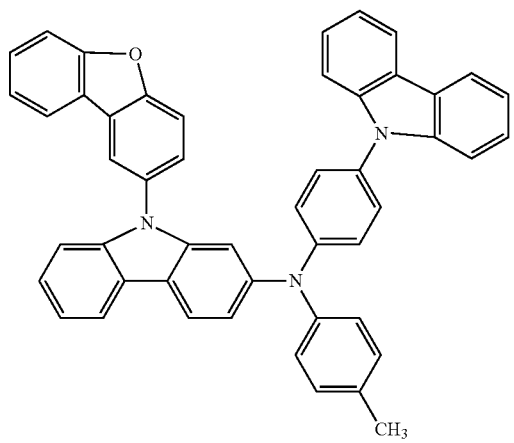
(B40)
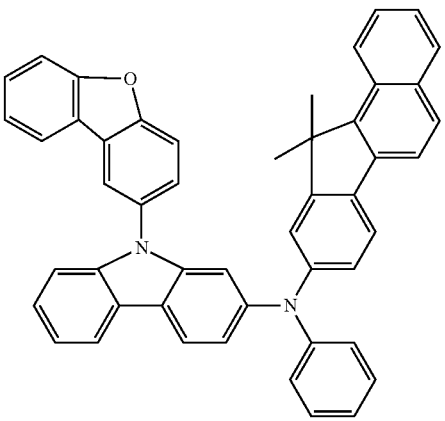
(B38)
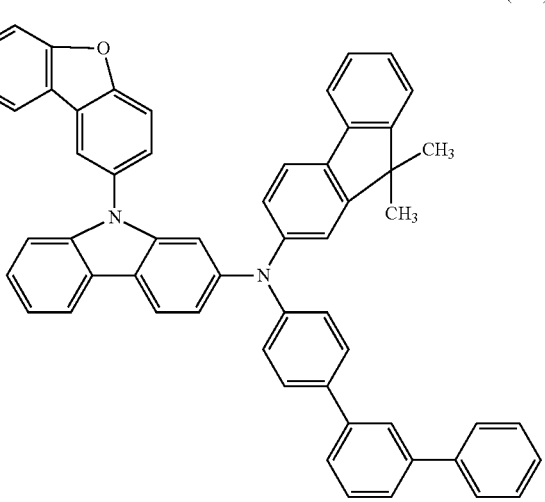
(B41)
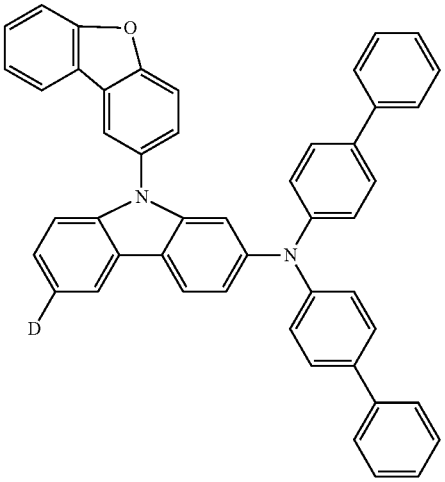
(B39)
(B42)
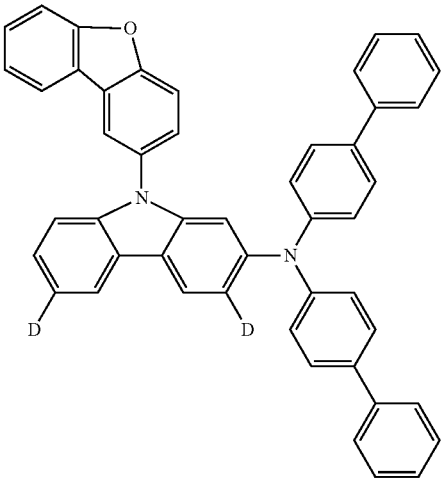

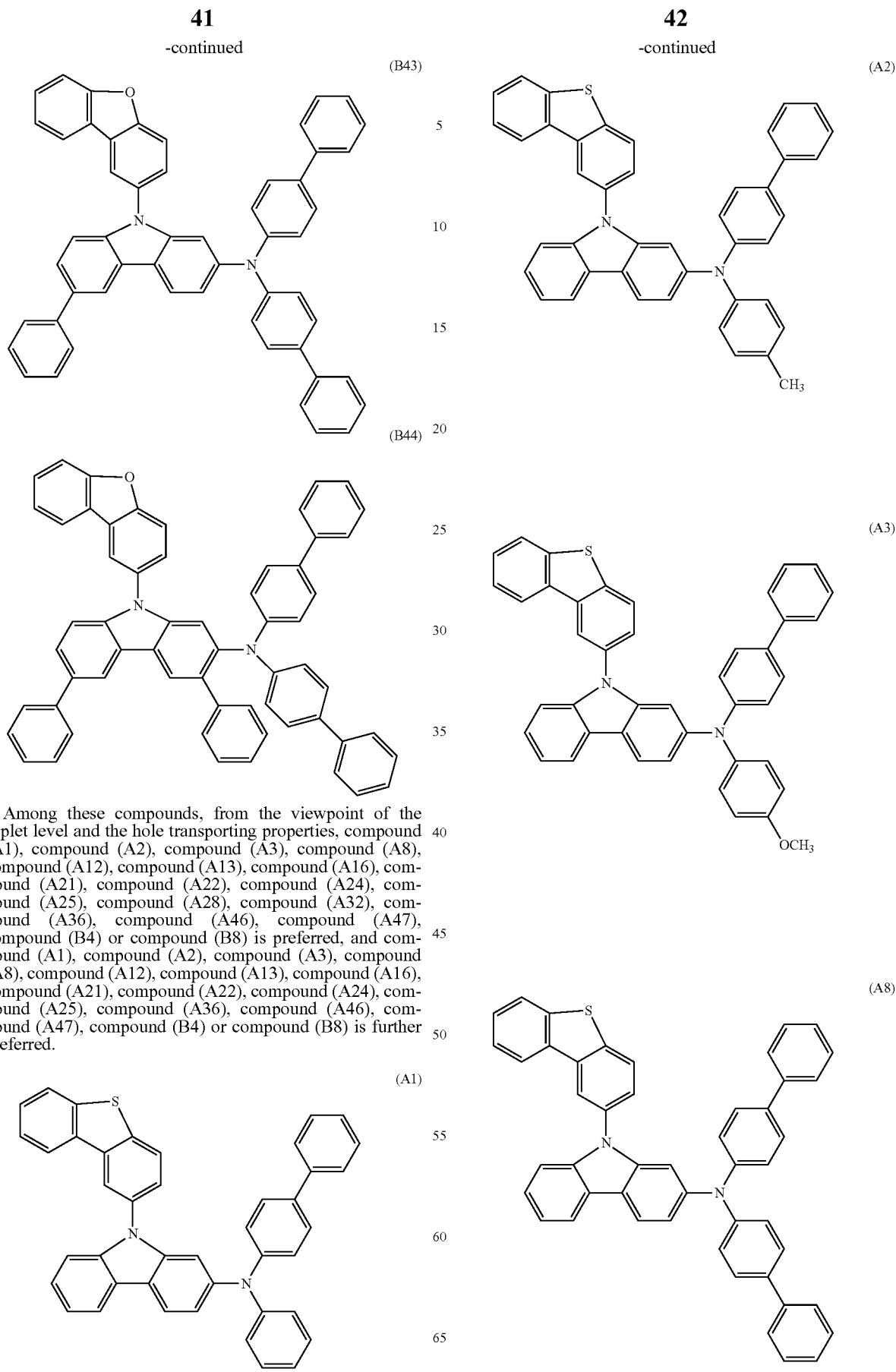

Among these compounds, from the viewpoint of the triplet level and the hole transporting properties, compound (A1), compound (A2), compound (A3), compound (A8), compound (A12), compound (A13), compound (A16), compound (A21), compound (A22), compound (A24), compound (A25), compound (A28), compound (A32), compound (A36), compound (A46), compound (A47), compound (B4) or compound (B8) is preferred, and compound (A1), compound (A2), compound (A3), compound (A8), compound (A12), compound (A13), compound (A16), compound (A21), compound (A22), compound (A24), compound (A25), compound (A36), compound (A46), compound (A47), compound (B4) or compound (B8) is further preferred.

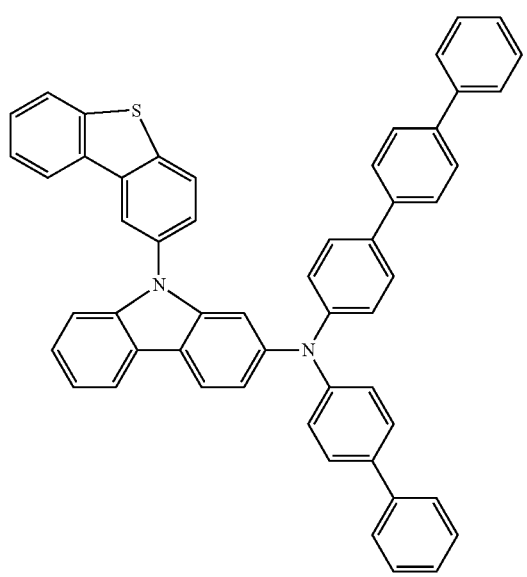
(A12)
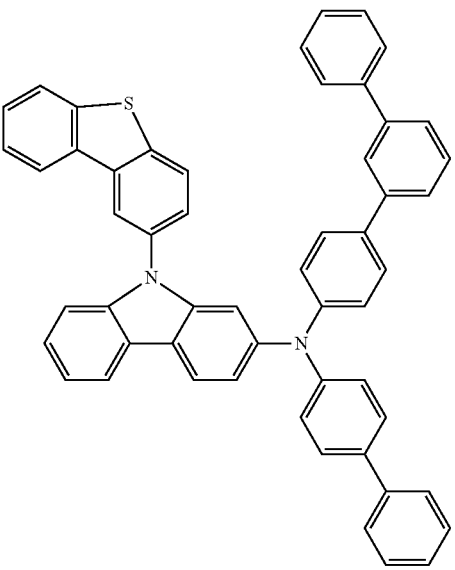
(A16)
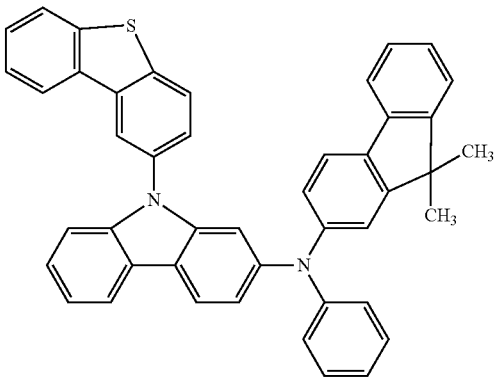
(A21)
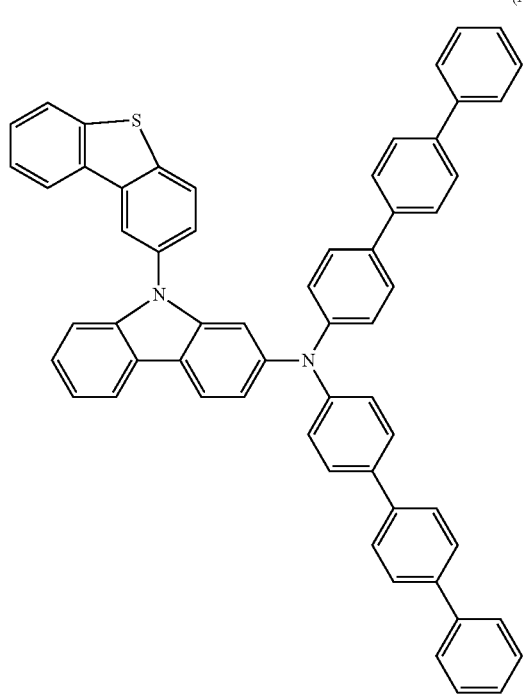
(A13)
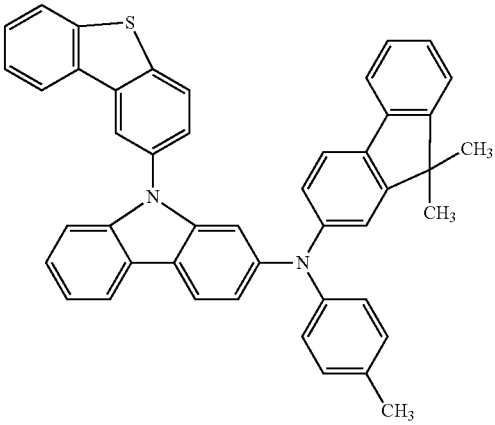
(A22)

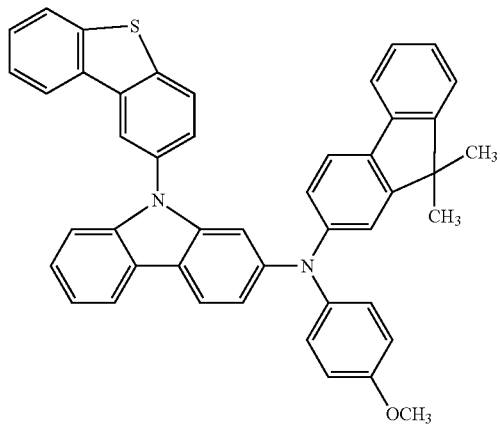 (A24)
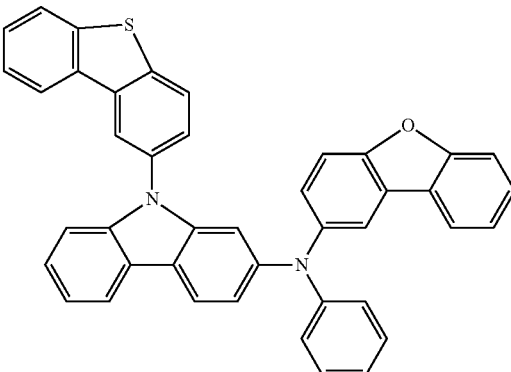 (A32)
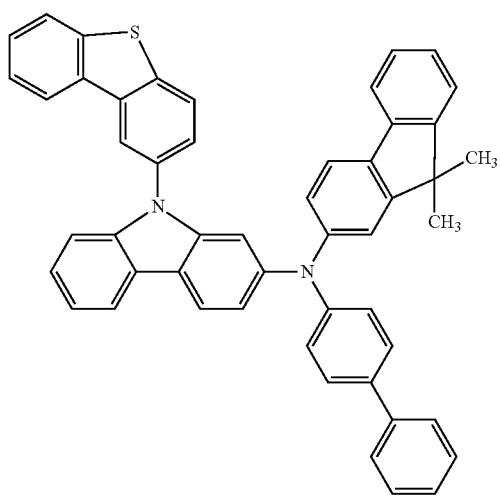 (A25)
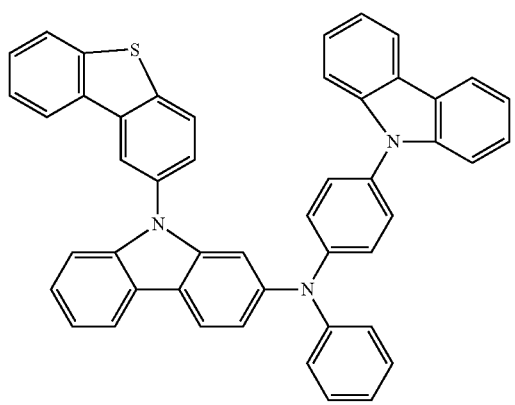 (A36)
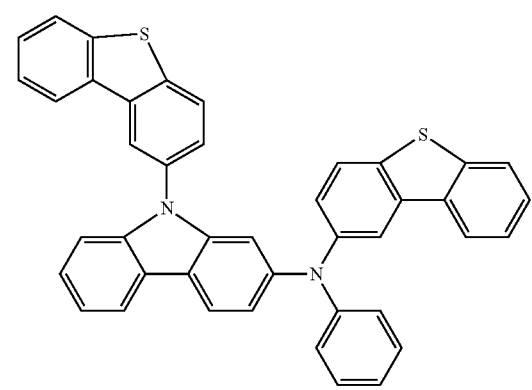 (A28)
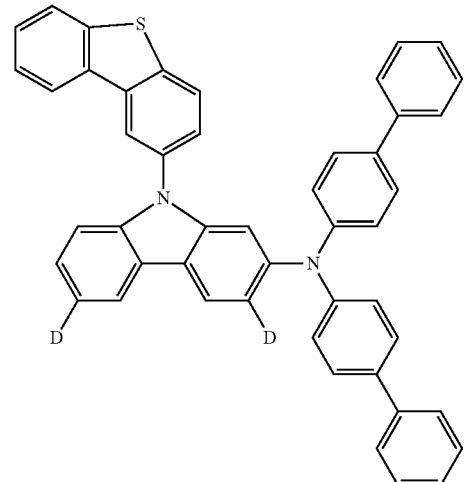 (A46)

-continued

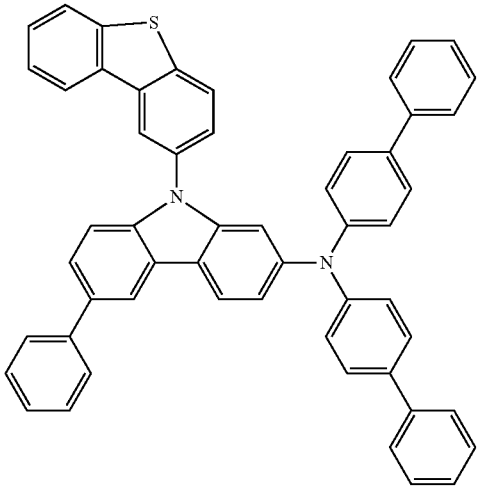

(A47)

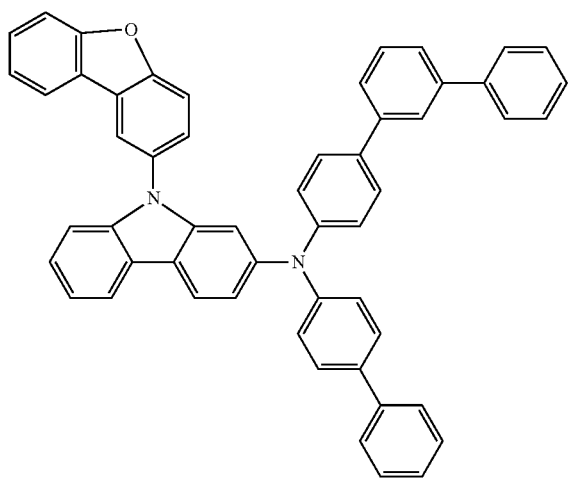

(B4)

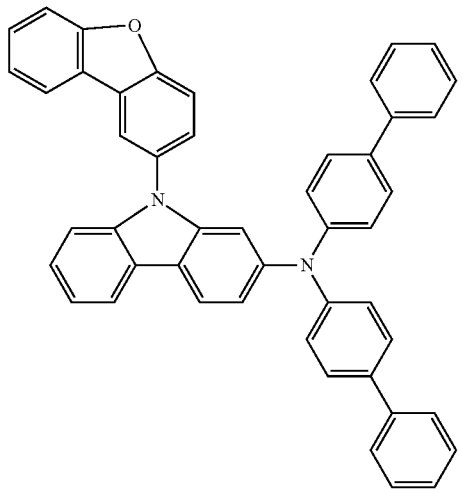

(B8)

The amine compound represented by the above formula (1) can be synthesized by a known method (Tetrahedron Letters, 1998, Vol. 39, p. 2367), by using e.g. a 9H-carbazole compound halogenated at the 2-position, as the starting material. Specifically, it can be synthesized by the following route.

A 9H-carbazole compound halogenated at the 2-position represented by the formula (2) and a compound having a halogen atom represented by the formula (3) are reacted by means of a copper catalyst or a palladium catalyst in the presence of a base to obtain a 2-halogenated-9-substituted carbazole compound represented by the formula (4). Further, the obtained 2-halogenated-9-substituted carbazole compound represented by the formula (4) and a secondary amine compound represented by the formula (5) are reacted by means of a copper catalyst or a palladium catalyst in the presence of a base.

In the above formulae (1) to (5), $Ar^1$, $Ar^2$, $R^1$ to $R^{10}$ and X represent the same definitions as in the above-described formula (1). Each of A and B which are independent of each other, is a halogen atom (iodine, bromine, chlorine or fluorine).

The compound represented by the formula (2) can be synthesized in accordance with a commonly known method (e.g. as disclosed in JP-A-2011-1349).

The compound represented by the formula (3) can be synthesized in accordance with a commonly known method (e.g. as disclosed in Journal of Heterocyclic Chemistry, 1987, Vol. 24, p. 749).

The compound represented by the formula (5) may be a commercially available compound, or can be synthesized in accordance with a commonly known method.

The amine compound represented by the formula (1) of the present invention can be used as a material for the luminescent layer, the hole transport layer or the hole injection layer of an organic EL device. Here, the amine compound represented by the formula (1) is preferably highly pure from the viewpoint of the hole transporting properties and the device lifetime.

Especially, the amine compound represented by the formula (1) may be suitably used in at least one layer among the hole injection layer, the hole transport layer and the luminescent layer in a device employing not only a fluorescent emitting material but also a phosphorescent emitting material in the luminescent layer.

In the luminescent layer at the time of using the amine compound represented by the formula (1) as a material for the hole injection layer and/or the hole transport layer of an organic EL device, a known fluorescent or phosphorescent emitting material which has been commonly used, may be employed. The luminescent layer may be formed solely of one type of luminescent material, or one or more luminescent materials may be doped in a host material.

At the time of forming a hole injection layer and/or a hole transport layer containing the amine compound represented by the formula (1), as the case requires, two or more materials may be co-deposited or laminated, and for example, known electron-accepting materials, such as an oxide such as molybdenum oxide, 7,7,8,8-tetracyanoquinodimethane, 2,3,5,6-tetrafluoro-7,7,8,8-tetracyanoquinodimethane, hexacyanohexaazatriphenylene, etc., may be co-deposited or laminated.

In a case where the amine compound represented by the formula (1) is to be used as a material for a luminescent layer of an organic EL device, the amine compound may be used alone, it may be used as a dopant material in a known luminescent host material, or it may be used as a host material with a known luminescent dopant.

As the method for forming a hole injection layer, a hole transport layer or a luminescent layer containing the amine compound represented by the formula (1), for example, a known method such as a vacuum vapor deposition method, a spin coating method or a casting method, may be employed.

EXAMPLES

Now, the present invention will be described in further detail with reference to Examples, but it should be understood that the present invention is by no means limited to these Examples.

$^1$H-NMR and $^{13}$C-NMR measurements were carried out by means of Gemini 200 manufactured by Varian Medical Systems Inc.

FDMS measurements were carried out by means of M-80B manufactured by Hitachi, Ltd.

The luminescence property of an organic EL device was evaluated by means of a luminance meter, LUMINANCEMETER (BM-9) manufactured by TOPCON Corporation, by applying direct current to a prepared device.

Preparation Example 1

Preparation of 2-chloro-9-(2-dibenzothienyl)carbazole

Under a nitrogen gas stream, into a 300 mL three-necked flask, 15.0 g (74.3 mmol) of 2-chlorocarbazole, 19.5 g (74.3 mmol) of 2-bromodibenzothiophene, 15.4 g (111.5 mmol) of potassium carbonate, 100 mL of o-xylene, 250 mg (1.1 mmol) of palladium acetate and 780 mg (3.9 mmol) of tri(tert-butyl)phosphine were added and stirred at 140° C. for 14 hours. After cooling to room temperature, 80 mL of pure water was added, and the organic layer was separated. The organic layer was washed with water and a saturated sodium chloride aqueous solution and then dried over anhydrous magnesium sulfate and concentrated under reduced pressure. The residue was purified by silica gel column chromatography (a mixed solvent of toluene and hexane (volume ratio=1:3)) to isolate 14.8 g (43.7 mmol) (yield: 62%) of a white powder of 2-chloro-9-(2-dibenzothienyl)carbazole.

Identification of the compound was conducted by $^1$H-NMR measurements and $^{13}$C-NMR measurements.

$^1$H-NMR(CDCl$_3$)δ(ppm); 8.22(d,1H),8.10(t,1H),8.61(t,1H),8.03(d,1H),7.99(d,1H), 7.85(ddd,1H),7.56-7.19(m,8H)

$^{13}$C-NMR(CDCl$_3$)δ(ppm); 141.37,141.17,139.78,138.44, 136.65,134.39,133.33, 131.33,126.98,125.84,125.26, 124.25,123.81,122.55,122.29,121.45,120.75,120.00, 119.85,109.45,109.38

Preparation Example 2

Preparation of 2-chloro-3,6-dibromo-9-(2-dibenzothienyl)carbazole

In a 200 mL three-necked flask, 6.2 g (16.3 mmol) of 2-chloro-9-(2-dibenzothienyl)carbazole obtained in Preparation Example 1 was dissolved in 60 mL of dichloromethane, and 2.9 g (16.3 mmol) of NBS was added, followed by stirring at room temperature for 30 minutes. The reaction solution was washed with pure water and a saturated sodium chloride aqueous solution, then dried over anhydrous magnesium sulfate and concentrated under reduced pressure. The residue was purified by silica gel column chromatography (a mixed solvent of toluene and hexane (volume ratio=1:5)) to isolate 5.5 g (10.2 mmol) (yield: 62%) of a white powder of 2-chloro-3,6-dibromo-9-(2-dibenzothienyl)carbazole.

Identification of the compound was conducted by $^1$H-NMR measurements and $^{13}$C-NMR measurements.

$^1$H-NMR(CDCl$_3$)δ(ppm); 8.33(d,1H),8.03-8.23(m,4H), 7.93(d,1H),7.46-7.55(m,6H)

$^{13}$C-NMR(CDCl$_3$)δ(ppm); 140.50,140.14,139.79,139.00, 136.71,134.15,132.45, 131.72,129.24,127.14,124.87, 124.48,124.32,124.01,122.76,122.56,121.41,119.65, 113.06,111.02,110.95

Preparation Example 3

Preparation of 2-chloro-3,6-d$_2$-9-(2-dibenzothienyl)carbazole

Under a nitrogen gas stream, in a 200 mL three-necked flask, 5.2 g (9.7 mmol) of 2-chloro-3,6-dibromo-9-(2-dibenzothienyl)carbazole obtained in Preparation Example 2 was dissolved in 100 mL of tetrahydrofuran, followed by cooling to −78° C. 14.2 mL (23.4 mmol) of a hexane solution of n-butyllithium (1.6 M) was dropwise added and stirred at −78° C. for 30 minutes, and then, 3.2 g (160 mmol) of deuterated water was further dropwise added. The reaction solution was brought to room temperature, then washed with water and a saturated sodium chloride aqueous solution, then dried over anhydrous magnesium sulfate and concentrated under reduced pressure. The residue was recrystallized in toluene to isolate 2.5 g (6.4 mmol) (yield: 66%) of a slightly yellow powder of 2-chloro-3,6-d$_2$-9-(2-dibenzothienyl)carbazole.

Identification of the compound was conducted by $^1$H-NMR measurements and $^{13}$C-NMR measurements.

$^1$H-NMR(CDCl$_3$)δ(ppm); 8.27(d,1H),8.03-8.12(m,4H), 7.90(d,1H),7.57(d,1H),7.44-7.52(m,2H),7.34-7.42(m,3H)

$^{13}$C-NMR(CDCl$_3$)δ(ppm); 141.37,141.16,139.75,138.44, 136.62,134.37,133.31, 131.22,126.65,125.69,125.27, 124.23,123.79,122.52,122.25,121.42,120.58,119.99, 119.85,119.70,109.39,109.32,97.49

Preparation Example 4

Preparation of 2-chloro-6-phenyl-9-(2-dibenzothienyl)carbazole

Under a nitrogen gas stream, into a 50 mL three-necked flask, 4.0 g (14.4 mmol) of 2-chloro-6-phenylcarbazole, 3.7 g (14.4 mmol) of 2-bromodibenzothiophene, 3.9 g (28.8 mmol) of potassium carbonate, 20 mL of o-xylene, 96 mg (0.43 mmol) of palladium acetate and 305 mg (1.5 mmol) of tri(tert-butyl)phosphine were added and stirred at 140° C. for 7 hours. After cooling to room temperature, 10 mL of pure water was added, and the organic layer was separated. The organic layer was washed with water and a saturated sodium chloride aqueous solution and then dried over anhydrous magnesium sulfate and concentrated under reduced pressure. The residue was purified by silica gel column chromatography (a mixed solvent of toluene and hexane (volume ratio=1:2)) to isolate 5.2 g (11.3 mmol) (yield: 78%) of a white powder of 2-chloro-6-phenyl-9-(2-dibenzothienyl)carbazole.

Identification of the compound was conducted by FDMS measurements.

FDMS (m/z); 459 (M+)

Preparation Example 5

Preparation of 2-chloro-9-(2-dibenzofuranyl)carbazole

Under a nitrogen gas stream, into a 50 mL three-necked flask, 2.8 g (14.2 mmol) of 2-chlorocarbazole, 3.5 g (14.2 mmol) of 2-bromodibenzofuran, 3.9 g (28.4 mmol) of potassium carbonate, 17 mL of o-xylene, 63 mg (0.28 mmol) of palladium acetate and 200 mg (0.99 mmol) of tri(tert-butyl) phosphine were added and stirred at 140° C. for 20 hours. After cooling to room temperature, 10 mL of pure water was added, and the organic layer was separated. The organic layer was washed with water and a saturated sodium chloride aqueous solution and then dried over anhydrous magnesium sulfate and concentrated under reduced pressure. The residue was purified by silica gel column chromatography (a mixed solvent of toluene and hexane (volume ratio=1:3)) to isolate 3.8 g (10.5 mmol) (yield: 74%) of a colorless viscous solid of 2-chloro-9-(2-dibenzofuranyl)carbazole.

Identification of the compound was conducted by FDMS and $^1$H-NMR measurements.

FDMS (m/z); 367 (M+)

$^1$H-NMR(CDCl$_3$)δ(ppm); 8.05(d,1H),7.92-7.98(m,2H), 7.83(t,2H),7.67(d,1H),7.18-7.59(m,8H)

Example 1

Preparation of Compound (A1)

Under a nitrogen gas stream, into a 50 mL three-necked flask, 3.4 g (8.8 mmol) of 2-chloro-9-(2-dibenzothienyl)carbazole obtained in Preparation Example 1, 2.3 g (9.7 mmol) of N-phenyl-N-biphenylamine, 1.1 g (12.4 mmol) of sodium tert-butoxide, 20 mL of o-xylene, 19 mg (0.08 mmol) of palladium acetate and 62 mg (0.30 mmol) of tri(tert-butyl)phosphine were added and stirred at 140° C. for 12 hours. After cooling to room temperature, 10 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 3.3 g (5.5 mmol) (yield: 62%) of a colorless glassy solid of compound (A1).

Identification of the compound was conducted by FDMS, $^1$H-NMR measurements and $^{13}$C-NMR measurements.

FDMS (m/z); 592 (M+)

$^1$H-NMR(CDCl$_3$)δ(ppm); 8.17(d,1H),8.05(t,2H),7.95(dt, 1H),7.92(d,1H), 7.82(d,1H)7.54(dd,1H),7.51-7.08(m,20H), 6.96(tt,1H)

$^{13}$C-NMR(CDCl$_3$)δ(ppm); 147.43,146.95,145.91,141.61, 141.10,140.10,139.69, 137.73,136.44,134.45,134.30, 133.77,128.72,127.16,126.78,126.23,126.10,124.93, 124.12,123.61,123.00,122.98,122.44,122.23,121.30,120.59, 119.82,119.34,119.03, 117.99,109.12,105.79

Example 2

Preparation of Compound (A2)

Under a nitrogen gas stream, into a 50 mL three-necked flask, 2.7 g (7.0 mmol) of 2-chloro-9-(2-dibenzothienyl)carbazole obtained in Preparation Example 1, 2.0 g (7.7 mmol) of N-(p-tolyl)-N-biphenylamine, 0.94 g (9.8 mmol) of sodium tert-butoxide, 15 mL of o-xylene, 22 mg (0.09 mmol) of palladium acetate and 69 mg (0.34 mmol) of tri(tert-butyl)phosphine were added and stirred at 140° C. for 18 hours. After cooling to room temperature, 10 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 3.3 g (5.5 mmol) (yield: 79%) of a colorless glassy solid of compound (A2).

Identification of the compound was conducted by FDMS, $^1$H-NMR measurements and $^{13}$C-NMR measurements.

FDMS (m/z); 606 (M+)

$^1$H-NMR(CDCl$_3$)δ(ppm); 8.15(d,1H),8.07-7.97(m,2H), 7.93(t,2H),7.81(d,1H), 7.54(dd,1H),7.49-6.98(m,20H),2.26 (s,3H)

$^{13}$C-NMR(CDCl$_3$)δ(ppm); 147.45,146.40,145.08,141.86, 141.31,140.43,139.97, 137.94,136.71,134.74,134.13, 134.10,132.50,129.70,128.46,127.36,127.05,126.42, 126.35,125.21,125.09,124.57,124.41,123.84,123.27,122.72, 121.53,120.78,120.07, 119.59,118.99,117.91,109.36, 105.49,20.78

Example 3

Preparation of Compound (A3)

Under a nitrogen gas stream, into a 50 mL three-necked flask, 3.0 g (7.9 mmol) of 2-chloro-9-(2-dibenzothienyl) carbazole obtained in Preparation Example 1, 2.4 g (8.7 mmol) of N-(p-methoxyphenyl)-N-biphenylamine, 1.0 g (9.8 mmol) of sodium tert-butoxide, 17 mL of o-xylene, 35 mg (0.15 mmol) of palladium acetate and 106 mg (0.52 mmol) of tri(tert-butyl)phosphine were added and stirred at 140° C. for 10 hours. After cooling to room temperature, 10 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 4.0 g (6.5 mmol) (yield: 82%) of a white powder of compound (A3).

Identification of the compound was conducted by FDMS, $^1$H-NMR measurements and $^{13}$C-NMR measurements.

FDMS (m/z); 622 (M+)

$^1$H-NMR(CDCl$_3$)δ(ppm); 8.19(d,1H),8.08-7.83(m,5H), 7.56(dd,1H),7.49-7.10(m,18H),6.81(d,2H),3.74(s,3H)

$^{13}$C-NMR(CDCl$_3$)δ(ppm); 156.11,147.85,146.77,142.10, 141.51,140.84,140.67, 140.20,138.15,136.94,134.96, 134.34,133.90,128.68,127.56,127.27,127.18,126.59, 126.52,125.40,125.24,124.67,124.07,123.54,122.97,122.11, 121.78,120.97,120,29, 119.80,118.94,117.60,114.78, 109.58,105.08,55.53

Example 4

Preparation of Compound (A8)

Under a nitrogen gas stream, into a 50 mL three-necked flask, 4.0 g (10.4 mmol) of 2-chloro-9-(2-dibenzothienyl) carbazole obtained in Preparation Example 1, 3.3 g (10.4 mmol) of N,N-dibiphenylamine, 1.4 g (14.6 mmol) of sodium tert-butoxide, 23 mL of o-xylene, 24 mg (0.11 mmol) of palladium acetate and 300 mg (0.37 mmol) of tri(tert-butyl)phosphine were added and stirred at 140° C. for 12 hours. After cooling to room temperature, the precipitated product was collected by filtration and washed with pure water and ethanol. It was recrystallized in o-xylene, and 5.3 g (7.9 mmol) (yield: 76%) of a white powder of compound (A8) was isolated.

Identification of the compound was conducted by FDMS and $^1$H-NMR measurements.

FDMS (m/z); 668 (M+)

$^1$H-NMR(CDCl$_3$)δ(ppm); 8.50(d,1H),8.09(t,2H),7.98(d, 1H),7.96(d,1H),7.84(d,1H), 7.58(dd,1H),7.54-7.13(m,25H)

Example 5

Preparation of Compound (A12)

Under a nitrogen gas stream, into a 50 mL three-necked flask, 2.9 g (7.5 mmol) of 2-chloro-9-(2-dibenzothienyl) carbazole obtained in Preparation Example 1, 3.0 g (7.5 mmol) of N-biphenyl-N-(p-terphenyl)amine, 1.0 g (10.6 mmol) of sodium tert-butoxide, 20 mL of o-xylene, 35 mg (0.15 mmol) of palladium acetate and 112 mg (0.55 mmol) of tri(tert-butyl)phosphine were added and stirred at 140° C. for 4 hours. After cooling to room temperature, the precipitated product was collected by filtration and washed with pure water and ethanol. It was recrystallized in o-xylene, and 3.9 g (5.2 mmol) (yield: 69%) of a slightly yellow powder of compound (A12) was isolated.

Identification of the compound was conducted by FDMS, $^1$H-NMR measurements and $^{13}$C-NMR measurements.

FDMS (m/z); 744 (M+)

$^1$H-NMR(CDCl$_3$)δ(ppm); 8.20(d,1H),8.09(t,2H),7.99(d, 1H),7.97(d,1H),7.84(d,1H), 7.14-7.65(m,30H)

$^{13}$C-NMR(CDCl$_3$)δ(ppm); 146.79,146.66,145.63,141.60, 141.11,140.19,140.03, 139.64,139.00,137.74,136.44, 134.65,134.39,133.73,128.27,128.18,127.21,127.06, 126.88,126.73,126.42,126.26,126.09,124.94,124.90,124.13, 123.58,123.37,123.26, 122.87,122.41,121.17,120.60, 119.79,119.37,119.33,119.18,118.04,115.97,109.12, 105.93

Example 6

Preparation of Compound (A13)

Under a nitrogen gas stream, into a 50 mL three-necked flask, 2.9 g (7.5 mmol) of 2-chloro-9-(2-dibenzothienyl) carbazole obtained in Preparation Example 1, 3.5 g (7.5 mmol) of N,N-bis(p-terphenyl)amine, 1.0 g (10.6 mmol) of sodium tert-butoxide, 20 mL of o-xylene, 35 mg (0.15 mmol) of palladium acetate and 112 mg (0.55 mmol) of tri(tert-butyl)phosphine were added and stirred at 140° C. for 6 hours. After cooling to room temperature, the precipitated product was collected by filtration and washed with pure water and ethanol. It was recrystallized in o-xylene, and 4.7 g (5.7 mmol) (yield: 76%) of a slightly yellow powder of compound (A13) was isolated.

Identification of the compound was conducted by FDMS, $^1$H-NMR measurements and $^{13}$C-NMR measurements.

FDMS (m/z); 820 (M+)

$^1$H-NMR(CDCl$_3$)δ(ppm); 8.20(d, 1H),8.09(t,2H),7.98(d, 1H),7.96(d,1H),7.83(d,1H), 7.19-7.65(m,34H)

$^{13}$C-NMR(CDCl$_3$)δ(ppm); 146.75,145.61,141.60,141.11, 140.18,139.64,139.00, 138.93,137.74,136.44,134.39, 134.02,133.73,128.27,127.08,126.90,126.73,126.45, 126.40,124.96,124.89,124.13,123.58,123.35,122.87,122.41, 121.17,120.64,119.81, 119.40,119.30,119.19,118.05, 109.14,105.93

Example 7

Preparation of Compound (A16)

Under a nitrogen gas stream, into a 50 mL three-necked flask, 4.0 g (10.4 mmol) of 2-chloro-9-(2-dibenzothienyl) carbazole obtained in Preparation Example 1, 4.1 g (10.4 mmol) of N-biphenyl-N-(m-terphenyl)amine, 1.4 g (14.6 mmol) of sodium tert-butoxide, 20 mL of o-xylene, 70 mg (0.31 mmol) of palladium acetate and 221 mg (1.0 mmol) of tri(tert-butyl)phosphine were added and stirred at 140° C. for 14 hours. After cooling to room temperature, 10 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 5.3 g (7.1 mmol) (yield: 68%) of a colorless glassy solid of compound (A16).

Identification of the compound was conducted by FDMS, $^1$H-NMR measurements and $^{13}$C-NMR measurements.

FDMS (m/z); 744 (M+)

$^1$H-NMR(CDCl$_3$)δ(ppm); 8.20(d,1H),8.09(t,2H),7.96(d,2H),7.82(d,1H),7.74(s,1H), 7.13-7.64(m,29H)

$^{13}$C-NMR(CDCl$_3$)δ(ppm); 146.86,146.69,145.65,141.60, 141.20,141.09,140.72, 140.61,140.05,139.63,137.72, 136.44,134.61,134.50,134.37,133.73,128.62,128.24, 128.18,127.32,127.21,126.83,126.73,126.26,126.11,125.16, 125.10,124.95,124.89, 124.13,123.58,123.29,122.87, 122.39,121.15,120.62,119.79,119.30,119.19,118.09, 109.12,105.97

Example 8

Preparation of Compound (A21)

Under a nitrogen gas stream, into a 50 mL three-necked flask, 1.9 g (4.9 mmol) of 2-chloro-9-(2-dibenzothienyl) carbazole obtained in Preparation Example 1, 1.5 g (5.4 mmol) of N-phenyl-N-(9,9-dimethylfluoren-2-yl)amine, 0.66 g (6.9 mmol) of sodium tert-butoxide, 10 mL of o-xylene, 11 mg (0.05 mmol) of palladium acetate and 34 mg (0.17 mmol) of tri(tert-butyl)phosphine were added and stirred at 140° C. for 18 hours. After cooling to room temperature, 10 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 2.4 g (3.7 mmol) (yield: 76%) of a white powder of compound (A21).

Identification of the compound was conducted by FDMS, $^1$H-NMR measurements and $^{13}$C-NMR measurements.

FDMS (m/z); 632 (M+)

$^1$H-NMR(CDCl$_3$)δ(ppm); 8.17(d,1H),8.05(t,2H),7.90(t,1H),7.80(d,1H),7.58(dt,1H), 7.52(d,1H),7.51(d,1H),7.44-6.91(m,18H),1.34(s,6H)

$^{13}$C-NMR(CDCl$_3$)δ(ppm); 154.66,153.21,148.03,147.43, 146.57,141.97,141.42, 139.92,138.82,138.05,136.73, 134.66,134.04,133.56,128.95,127.06,126.75,126.15, 125.21,125.12,124.34,123.84,123.66,123.24,122.25,121.57, 120.80,120.07,119.70, 119.59,119.15,119.01,118.02,117.87, 109.41,105.66

Example 9

Preparation of Compound (A22)

Under a nitrogen gas stream, into a 50 mL three-necked flask, 5.0 g (13.0 mmol) of 2-chloro-9-(2-dibenzothienyl) carbazole obtained in Preparation Example 1, 4.2 g (14.3 mmol) of N-(p-tolyl)-N-(9,9-dimethylfluoren-2-yl)amine, 1.7 g (18.2 mmol) of sodium tert-butoxide, 25 mL of o-xylene, 58 mg (0.26 mmol) of palladium acetate and 184 mg (0.91 mmol) of tri(tert-butyl)phosphine were added and stirred at 140° C. for 16 hours. After cooling to room temperature, 15 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 6.4 g (9.9 mmol) (yield: 75%) of a slightly yellow powder of compound (A22).

Identification of the compound was conducted by FDMS, $^1$H-NMR measurements and $^{13}$C-NMR measurements.

FDMS (m/z); 646 (M+)

$^1$H-NMR(CDCl$_3$)δ(ppm); 8.19(d,1H),8.07(d,1H),8.02(d,1H),7.99-7.94(m,1H),7.90(d,1H),7.61-7.21(m,14H),7.06(t,6H),2.28(s,3H),1.34(s,6H)

$^{13}$C-NMR(CDCl$_3$)δ(ppm); 154.26,152.87,147.34,146.50, 145.12,141.68,141.10, 139.65,138.59,137.71,136.43, 134.41,133.81,132.84,131.89,129.34,126.74,126.41, 125.71,124.98,124.69,124.05,123.99,123.53,122.99,122.42, 121.91,121,81,121.25, 120.39,119.93,119.71,119.43,119, 21,118.76,118.37,117.38,117.00,109.07,104,80,46.33, 26.67,20,48

Example 10

Preparation of Compound (A24)

Under a nitrogen gas stream, into a 50 mL three-necked flask, 4.5 g (11.7 mmol) of 2-chloro-9-(2-dibenzothienyl) carbazole obtained in Preparation Example 1, 4.0 g (12.9 mmol) of N-(p-methoxyphenyl)-N-(9,9-dimethylfluoren-2-yl)amine, 1.5 g (16.4 mmol) of sodium tert-butoxide, 25 mL of o-xylene, 52 mg (0.23 mmol) of palladium acetate and 165 mg (0.81 mmol) of tri(tert-butyl)phosphine were added and stirred at 140° C. for 10 hours. After cooling to room temperature, 15 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 6.3 g (9.5 mmol) (yield: 81%) of a white powder of compound (A24).

Identification of the compound was conducted by FDMS, $^1$H-NMR measurements and $^{13}$C-NMR measurements.

FDMS (m/z); 662 (M+)

$^1$H-NMR(CDCl$_3$)δ(ppm); 8.18(d,1H),8.05(dd,1H),8.09 (d,1H),7.95(dd,1H), 7.88(d,1H),7.82(d,1H),7.58-7.03(m, 16H),6.94(dd,1H),6.80(dt,2H),3.74(s,3H),1.33(s,6H)

$^{13}$C-NMR(CDCl$_3$)δ(ppm); 155.42,154.24,152.80,147.54, 146.68,141.74,141.11, 140.71,139.65,138.64,137.74, 136.43,134.41,133.83,132.42,126.76,126.43,125.64, 125.00,124.62,124.08,123.53,123.04,122,44,121.91,121.28, 121.01,120.39,119.93, 119.73,119.47,119.16,118.70,118.08, 116.83,116.16,114.20,109.07,104.07,55.01,46.31, 26.70

Example 11

Preparation of Compound (A25)

Under a nitrogen gas stream, into a 50 mL three-necked flask, 4.2 g (11.0 mmol) of 2-chloro-9-(2-dibenzothienyl) carbazole obtained in Preparation Example 1, 4.0 g (11.0 mmol) of N-biphenyl-N-(9,9-dimethylfluoren-2-yl)amine, 1.4 g (15.4 mmol) of sodium tert-butoxide, 20 mL of o-xylene, 74 mg (0.33 mmol) of palladium acetate and 234 mg (1.15 mmol) of tri(tert-butyl)phosphine were added and stirred at 140° C. for 12 hours. After cooling to room temperature, 10 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 5.2 g (7.3 mmol) (yield: 66%) of a slightly yellow powder of compound (A25).

Identification of the compound was conducted by FDMS and $^1$H-NMR measurements.

FDMS (m/z); 708 (M+)

$^1$H-NMR(CDCl$_3$)$\delta$(ppm);8.19(d,1H),8.04(t,2H),7.75-7.91(m,3H),6.95-7.59(m,24H),1.34(s,6H)

Example 12

Preparation of Compound (A28)

Under a nitrogen gas stream, into a 50 mL three-necked flask, 4.0 g (10.4 mmol) of 2-chloro-9-(2-dibenzothienyl)carbazole obtained in Preparation Example 1, 3.1 g (11.4 mmol) of N-(2-dibenzothienyl)-N-phenylamine, 1.4 g (14.6 mmol) of sodium tert-butoxide, 20 mL of o-xylene, 46 mg (0.20 mmol) of palladium acetate and 105 mg (0.52 mmol) of tri(tert-butyl)phosphine were added and stirred at 140° C. for 15 hours. After cooling to room temperature, 15 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 5.9 g (9.4 mmol) (yield: 90%) of a colorless glassy solid of compound (A28).

Identification of the compound was conducted by FDMS, $^1$H-NMR measurements and $^{13}$C-NMR measurements.

FDMS (m/z); 622 (M+)

$^1$H-NMR(CDCl$_3$)$\delta$(ppm); 8.16(d,1H),8.01-8.10(m,2H),7.77-7.93(m,6H),7.65(d,1H),7.55(d,1H),7.09-7.46(m,14H),6.95(t,1H)

$^{13}$C-NMR(CDCl$_3$)$\delta$(ppm); 147.85,146.31,144.99,141.60, 141.07,139.70,139.61, 137.67,136.40,136.17,134.76, 134.37,133.71,133.05,128.68,126.72,126.20,124.83, 124.04,123.97,123.71,123.55,122.91,122.85,122.36,121.81, 121.20,120.58,119.78, 119.29,119.25,118.82,117.63,116.64, 109.10,105.31

Example 13

Preparation of Compound (A32)

Under a nitrogen gas stream, into a 50 mL three-necked flask, 4.0 g (10.4 mmol) of 2-chloro-9-(2-dibenzothienyl)carbazole obtained in Preparation Example 1, 2.9 g (11.4 mmol) of N-(2-dibenzofuranyl)-N-phenylamine, 1.4 g (14.6 mmol) of sodium tert-butoxide, 20 mL of o-xylene, 46 mg (0.20 mmol) of palladium acetate and 105 mg (0.52 mmol) of tri(tert-butyl)phosphine were added and stirred at 140° C. for 10 hours. After cooling to room temperature, 15 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 5.8 g (9.5 mmol) (yield: 91%) of a colorless glassy solid of compound (A32).

Identification of the compound was conducted by FDMS, $^1$H-NMR measurements and $^{13}$C-NMR measurements.

FDMS (m/z); 606 (M+)

$^1$H-NMR(CDCl$_3$)$\delta$(ppm); 8.14(d,1H),7.99-8.08(m,2H), 7.72-7.90(m,5H),7.48-7.55(m,2H),7.08-7.42(m,15H),6.90 (t,1H)

$^{13}$C-NMR(CDCl$_3$)$\delta$(ppm); 156.27,152.19,148.23,146.71, 143.09,141.64,141.05, 139.61,137.65,136.42,134.39, 133.77,128.64,126.73,125.05,124.85,124.78,124.68, 124.02,123.66,123.55,123.00,122.39,122.21,122.12,121.35, 121.20,120.53,120.29, 119.79,119.26,118.53,117.27, 117.01,111.83,111.22,109.10,104.85

Example 14

Preparation of Compound (A36)

Under a nitrogen gas stream, into a 50 mL three-necked flask, 4.0 g (10.4 mmol) of 2-chloro-9-(2-dibenzothienyl)carbazole obtained in Preparation Example 1, 3.8 g (11.4 mmol) of N-(4-(9-carbazolyl)phenyl)-N-phenylamine, 1.4 g (14.6 mmol) of sodium tert-butoxide, 20 mL of o-xylene, 46 mg (0.20 mmol) of palladium acetate and 105 mg (0.52 mmol) of tri(tert-butyl)phosphine were added and stirred at 140° C. for 12 hours. After cooling to room temperature, 15 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 5.2 g (7.6 mmol) (yield: 73%) of a colorless glassy solid of compound (A36).

Identification of the compound was conducted by FDMS, $^1$H-NMR measurements and $^{13}$C-NMR measurements.

FDMS (m/z); 681 (M+)

$^1$H-NMR(CDCl$_3$)$\delta$(ppm); 8.53(d,1H),8.39-8.44(m,4H), 8.28(d,2H),8.15(d,1H), 7.88(d,1H),7.47-7.75(m,21H),7.33 (t,1H)

$^{13}$C-NMR(CDCl$_3$)$\delta$(ppm); 147.24,146.90,145.67,141.68, 141.16,140.52,139.64, 137.83,136.49,134.35,133.73, 130.65,128.86,127.28,126.83,125.31,125.03,124.94, 124.12,123.86,123.57,123.18,122.83,122.65,122.43,121.22, 120.73,119.83,119.70, 119.41,119.34,119.17,118.11,109.30, 109.14,106.12

Example 15

Preparation of Compound (A46)

Under a nitrogen gas stream, into a 50 mL three-necked flask, 3.2 g (8.4 mmol) of 2-chloro-3,6-d$_2$-9-(2-dibenzothienyl)carbazole obtained in Preparation Example 3, 2.7 g (8.4 mmol) of N,N-bisbiphenylamine, 1.1 g (11.7 mmol) of sodium tert-butoxide, 20 mL of o-xylene, 18 mg (0.08 mmol) of palladium acetate and 59 mg (0.29 mmol) of tri(tert-butyl)phosphine were added and stirred at 140° C. for 14 hours. After cooling to room temperature, the precipitated product was collected by filtration and washed with pure water and ethanol. It was recrystallized in o-xylene, and 4.4 g (6.6 mmol) (yield: 79%) of a white powder of compound (A46) was isolated.

Identification of the compound was conducted by FDMS and $^1$H-NMR measurements.

FDMS (m/z); 670 (M+)
$^1$H-NMR(CDCl$_3$)δ(ppm); 8.26(d,1H),8.03-8.13(m,4H), 7.91(d,1H),7.16-7.64(m,24H)

Example 16

Preparation of Compound (A47)

Under a nitrogen gas stream, into a 50 mL three-necked flask, 5.0 g (10.8 mmol) of 2-chloro-6-phenyl-9-(2-dibenzothienyl)carbazole obtained in Preparation Example 4, 3.6 g (11.4 mmol) of N,N-bisbiphenylamine, 1.4 g (15.2 mmol) of sodium tert-butoxide, 25 mL of o-xylene, 73 mg (0.32 mmol) of palladium acetate and 230 mg (1.14 mmol) of tri(tert-butyl)phosphine were added and stirred at 140° C. for 10 hours. After cooling to room temperature, the precipitated product was collected by filtration and washed with pure water and ethanol. It was recrystallized in o-xylene, and 4.9 g (6.5 mmol) (yield: 60%) of a white powder of compound (A47) was isolated.

Identification of the compound was conducted by FDMS, $^1$H-NMR measurements and $^{13}$C-NMR measurements.

FDMS (m/z); 744 (M+)
$^1$H-NMR(CDCl$_3$)δ(ppm); 8.29(d,1H),8.17(d,1H),8.08(d,1H),7.94(d,1H),7.91(d,1H), 7.81(d,1H),7.70(d,2H),7.12-7.60(m,28H)
$^{13}$C-NMR(CDCl$_3$)δ(ppm); 146.69,145.93,142.06,141.42, 140.58,140.05,139.68, 137.78,136.48,134.70,134.39, 133.71,133.35,128.29,128.22,127.25,126.79,126.31, 126.13,124.79,124.46,124.19,123.64,123.46,122.43,121.22, 120.69,119.21,118.05, 117.85,109.39,105.84

Example 17

Preparation of Compound (B4)

Under a nitrogen gas stream, into a 50 mL three-necked flask, 1.9 g (5.2 mmol) of 2-chloro-9-(2-dibenzofuranyl) carbazole obtained in Preparation Example 5, 2.0 g (5.2 mmol) of N-biphenyl-N-(m-terphenyl)amine, 0.7 g (7.3 mmol) of sodium tert-butoxide, 10 mL of o-xylene, 35 mg (0.15 mmol) of palladium acetate and 110 mg (0.5 mmol) of tri(tert-butyl)phosphine were added and stirred at 140° C. for 5 hours. After cooling to room temperature, 5 mL of pure water was added and stirred. The aqueous layer and the organic layer were separated, and the organic layer was further washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:2)) to isolate 3.0 g (4.2 mmol) (yield: 81%) of a colorless glassy solid of compound (B4).

Identification of the compound was conducted by FDMS and $^1$H-NMR measurements.

FDMS (m/z); 728 (M+)
$^1$H-NMR(CDCl$_3$)δ(ppm); 8.04-8.12(m,3H),7.84(d,1H), 7.69(d,1H),7.13-7.60(m,31H)

Example 18

Preparation of Compound (B8)

Under a nitrogen gas stream, into a 50 mL three-necked flask, 3.6 g (9.7 mmol) of 2-chloro-9-(2-dibenzofuranyl) carbazole obtained in Preparation Example 5, 2.8 g (9.7 mmol) of N,N-dibiphenylamine, 1.3 g (13.7 mmol) of sodium tert-butoxide, 20 mL of o-xylene, 66 mg (0.29 mmol) of palladium acetate and 207 mg (1.0 mmol) of tri(tert-butyl)phosphine were added and stirred at 140° C. for 6 hours. After cooling to room temperature, the precipitated product was collected by filtration and washed with pure water and ethanol. It was recrystallized in o-xylene, and 3.6 g (7.0 mmol) (yield: 72%) of a white powder of compound (B8) was isolated.

Identification of the compound was conducted by FDMS and $^1$H-NMR measurements.

FDMS (m/z); 652 (M+)
$^1$H-NMR(CDCl$_3$); 8.10(dt,1H),8.07(d,1H),8.02(d,1H), 7.84(dt,1H),7.70(dd,1H),7.61-7.12(m,27H)

Comparative Example 1

Preparation of Compound (b)

Under a nitrogen gas stream, into a 50 mL three-necked flask, 0.50 g (1.2 mmol) of 3-bromo-9-(2-dibenzofuranyl) carbazole prepared in accordance with a known literature (WO2011/122132), 0.05 g (0.60 mmol) of aniline, 0.16 g (1.6 mmol) of sodium tert-butoxide, 10 mL of o-xylene, 5 mg (0.02 mmol) of palladium acetate and 14 mg (0.07 mmol) of tri(tert-butyl)phosphine were added and stirred at 140° C. for 3 hours. After cooling to room temperature, 5 mL of pure water was added, and the organic layer was separated. The organic layer was washed with pure water and a saturated sodium chloride aqueous solution. The organic layer was dried over anhydrous magnesium sulfate and then, concentrated under reduced pressure. The residue was purified by silica gel column chromatography (a mixed solvent of toluene and hexane (volume ratio=1:1)) to isolate 0.35 g (0.47 mmol) (yield: 79%) of a colorless glassy solid of compound (b).

Identification of the compound was conducted by FDMS measurements.

FDMS (m/z); 755 (M+)

Example 19

Device Evaluation of Compound (A1)

A glass substrate having an ITO transparent electrode (anode) with a thickness of 200 nm laminated thereon, was subjected to ultrasonic cleaning with acetone and pure water and to boiling cleaning with isopropyl alcohol. Further, it was subjected to ultraviolet ray/ozone cleaning and then set in a vacuum vapor deposition equipment, which was then evacuated to 1×10$^{-4}$ Pa by means of a vacuum pump. Firstly, on the ITO transparent electrode, copper phthalocyanine was vapor-deposited at a vapor-deposition rate of 0.1 nm/sec. to form a hole injection layer of 10 nm, and then, compound (A1) was vapor-deposited at a vapor-deposition rate of 0.3 nm/sec in a thickness of 30 nm to form a hole transport layer. Then, tris(2-phenylpyridine)iridium (Ir(ppy)$_3$) as a phosphorescent dopant and 4,4'-bis(N-carbazolyl) biphenyl (CBP) as a host material were co-vapor-deposited at a vapor-deposition rate of 0.25 nm/sec so that their weight ratio would be 1:11.5 to form a luminescent layer of 30 nm. Then, BAlq (bis(2-methyl-8-quinolinolato) (p-phenyl phenolate) aluminum) was vapor-deposited at a vapor-deposition rate of 0.3 nm/sec to form an exciton blocking layer of 5 nm, and then, Alq$_3$ (tris(8-quinolinolato) aluminum) was vapor-deposited at 0.3 nm/sec to form an electron transport layer of 45 nm. Then, as an electron injection layer, lithium fluoride was further vapor-deposited at a vapor-deposition rate of 0.01 nm/sec in a thickness of 1 nm, and further, aluminum was vapor-deposited at a vapor-deposition rate of 0.25 nm/sec in a thickness of 100 nm to form a cathode. In a nitrogen atmosphere, a sealing glass sheet was bonded by a UV curable resin to obtain an organic EL device for evaluation. To the device thus prepared, an electric current of 20 mA/cm² was applied, whereby the driving voltage and the current efficiency were measured. Further, the luminance half-life time of the device was evaluated by applying an electric current of 6.25 mA/cm². The results are shown in Table 1.

Examples 20 to 36

Device Evaluation

An organic EL device was prepared in the same manner as in Example 19 except that compound (A1) was changed to compound (A2), (A3), (A8), (A12), (A13), (A16), (A21), (A22), (A24), (A25), (A28), (A32), (A36), (A46), (A47), (B4) or (B8). The driving voltage and the current efficiency when an electric current of 20 mA/cm² was applied, and the luminance half-life time of the device when an electric current of 6.25 mA/cm² was applied, are shown in Table 1.

Comparative Example 2

Device Evaluation of NPD

An organic EL device was prepared in the same manner as in Example 19 except that compound (A1) was changed to NPD (4,4'-bis[N-(1-naphthyl)-N-phenylamino]biphenyl). The driving voltage and the current efficiency when an electric current of 20 mA/cm² was applied, and the luminance half-life time of the device when an electric current of 6.25 mA/cm² was applied, are shown in Table 1.

Comparative Example 3

Device Evaluation of Compound (b)

An organic EL device was prepared in the same manner as in Example 19 except that compound (A1) was changed to the following compound (b). The driving voltage and the current efficiency when an electric current of 20 mA/cm² was applied, and the luminance half-life time of the device when an electric current of 6.25 mA/cm² was applied, are shown in Table 1.

Reference Example 1

Device Evaluation of Compound (a)

An organic EL device was prepared in the same manner as in Example 19 except that compound (A1) was changed to the following compound (a). The driving voltage and the current efficiency when an electric current of 20 mA/cm² was applied, and the luminance half-life time of the device when an electric current of 6.25 mA/cm² was applied, are shown in Table 1.

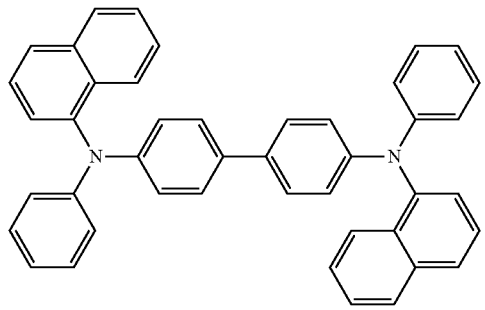

NPD

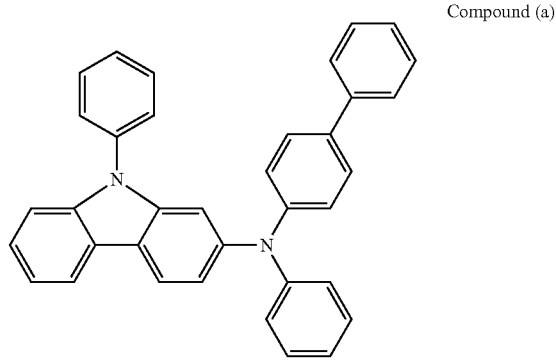

Compound (a)

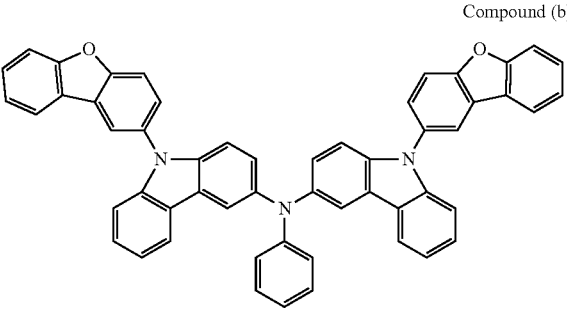

Compound (b)

TABLE 1

| | Compound (hole transport layer) | Driving voltage (V) | Current efficiency (cd/A) | Luminance half-life time (hr) |
|---|---|---|---|---|
| Example 19 | (A1) | 8.4 | 38 | 1940 |
| Example 20 | (A2) | 8.1 | 37 | 1890 |
| Example 21 | (A3) | 7.9 | 38 | 1810 |
| Example 22 | (A8) | 7.8 | 39 | 2060 |
| Example 23 | (A12) | 7.9 | 34 | 2360 |
| Example 24 | (A13) | 7.7 | 33 | 2530 |
| Example 25 | (A16) | 7.9 | 39 | 1980 |
| Example 26 | (A21) | 7.9 | 38 | 2170 |
| Example 27 | (A22) | 7.8 | 37 | 1890 |
| Example 28 | (A24) | 7.7 | 37 | 1950 |
| Example 29 | (A25) | 8.0 | 38 | 1990 |
| Example 30 | (A28) | 8.2 | 39 | 2110 |
| Example 31 | (A32) | 8.3 | 38 | 1870 |
| Example 32 | (A36) | 8.3 | 40 | 1920 |
| Example 33 | (A46) | 7.9 | 40 | 2190 |
| Example 34 | (A47) | 8.0 | 39 | 2100 |
| Example 35 | (B4) | 7.8 | 40 | 1900 |
| Example 36 | (B8) | 8.0 | 37 | 1880 |
| Comparative Example 2 | NPD | 8.7 | 28 | 1310 |
| Comparative Example 3 | Compound (b) | 8.9 | 30 | 1260 |
| Reference Example 1 | Compound (a) | 8.5 | 37 | 1480 |

INDUSTRIAL APPLICABILITY

The amine compound of the present invention is useful for the production of organic EL devices.

The entire disclosures of Japanese Patent Application No. 2012-214844 filed on Sep. 27, 2012 and Japanese Patent Application No. 2013-119485 filed on Jun. 6, 2013 including specifications, claims and summaries are incorporated herein by reference in their entireties.

The invention claimed is:

1. An amine compound of formula (1):

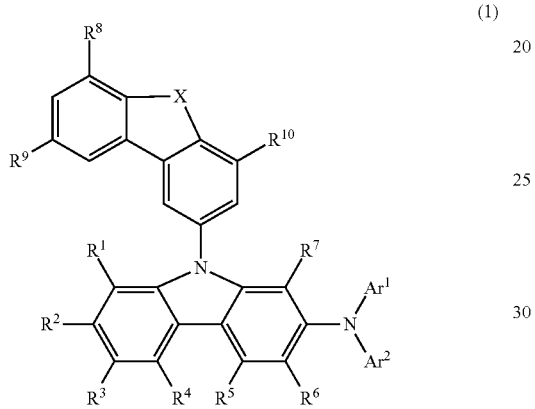

(1)

wherein X is a sulfur atom or an oxygen atom, each of $R^1$ to $R^{10}$ which are independent of one another, is a hydrogen atom, a deuterium atom or a phenyl group, and each of $Ar^1$ and $Ar^2$ which are independent of each other, is a $C_{6-18}$ aromatic hydrocarbon group, a dibenzothienyl group or a dibenzofuranyl group, which, each independently, may have a substituent consisting of a methyl group, a methoxy group, a dibenzothienyl group, a dibenzofuranyl group or a 9-carbazolyl group;

wherein the amine compound is represented by one of the following formulae:

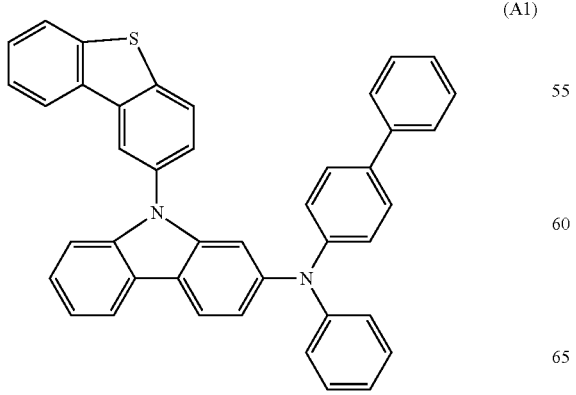

(A1)

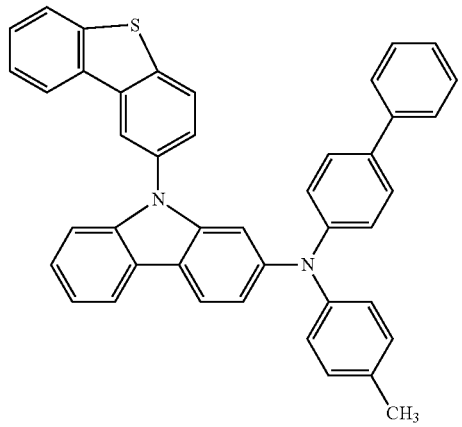

(A2)

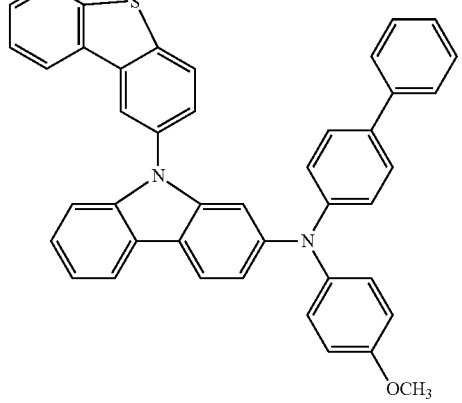

(A3)

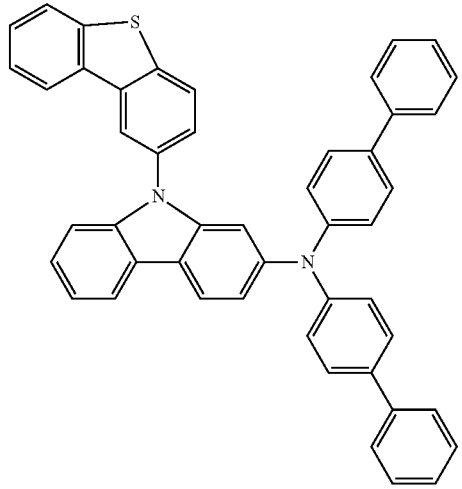

(A8)

(A12)
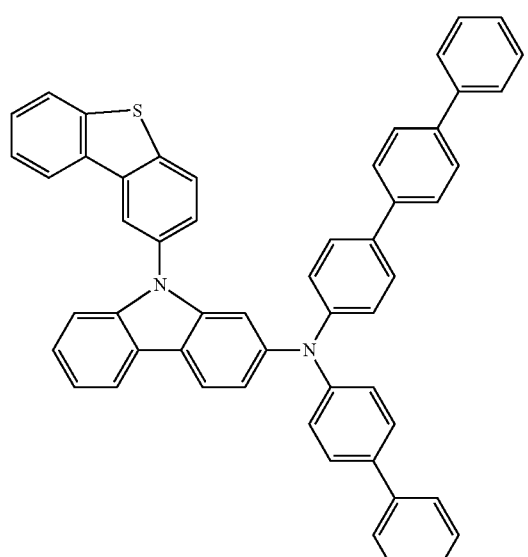
(A13)
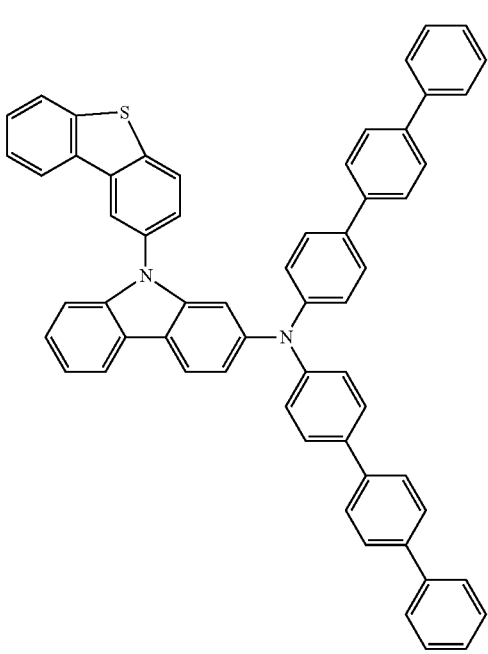
(A16)
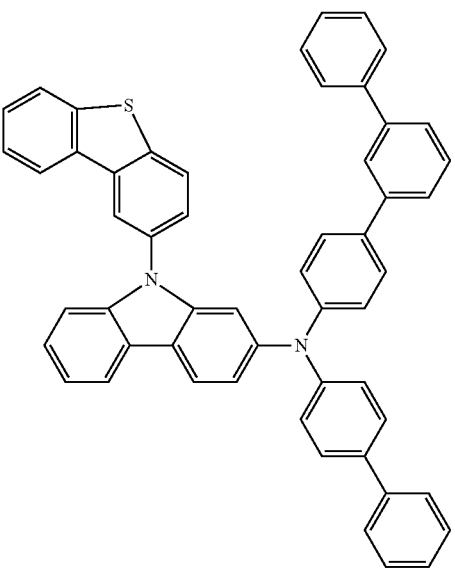
(A21)
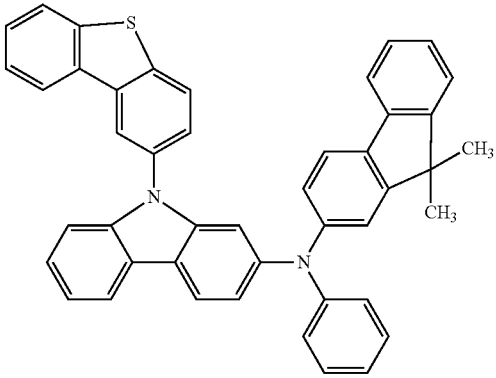
(A22)
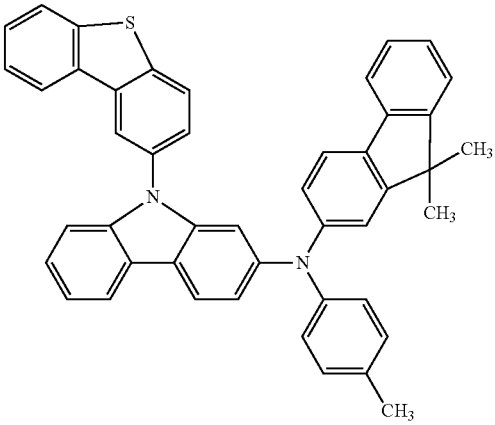

-continued
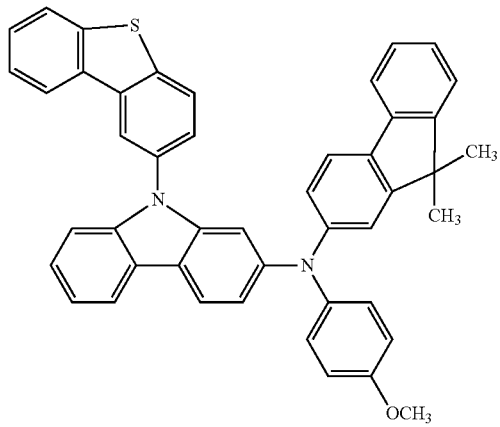
(A24)
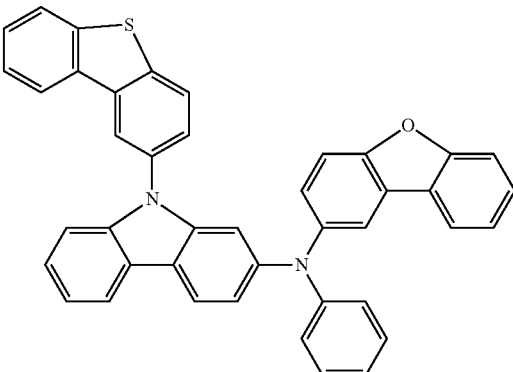
(A32)
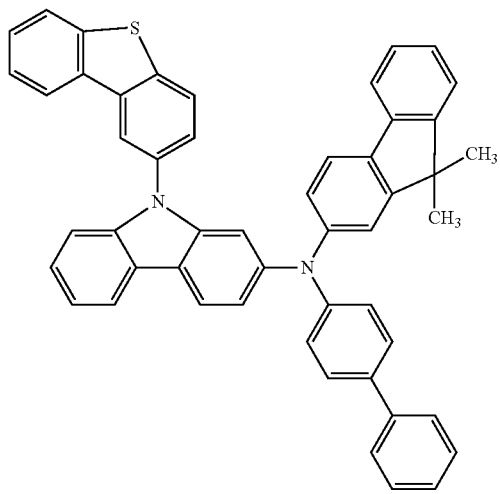
(A25)
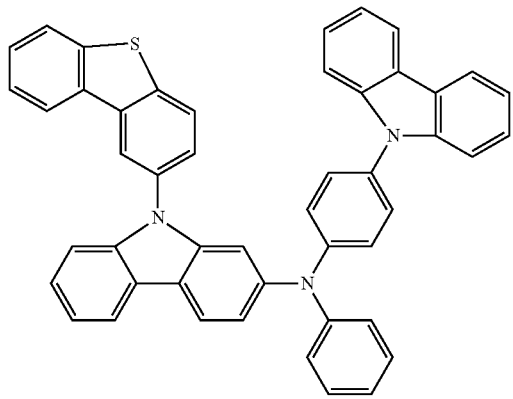
(A36)
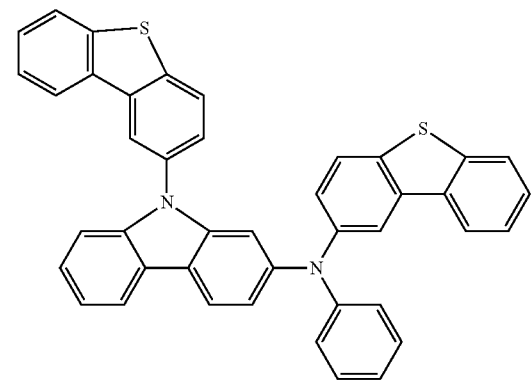
(A28)
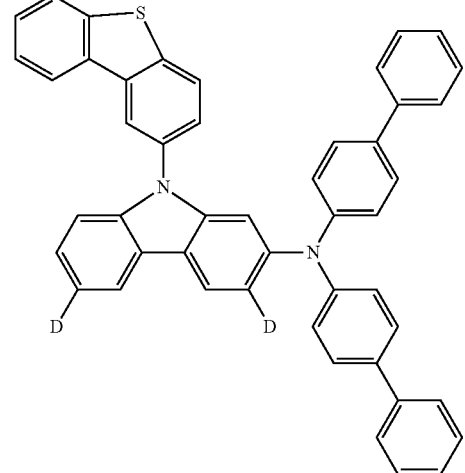
(A46)

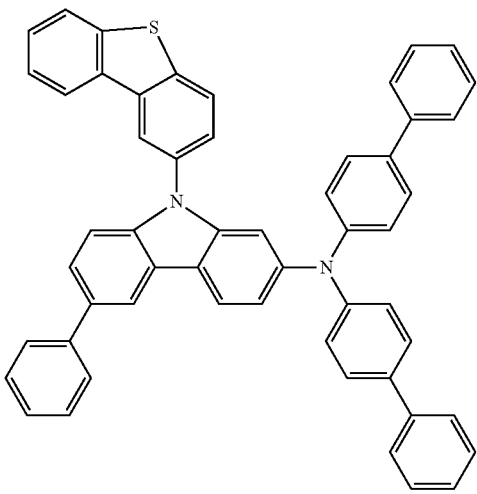 (A47)

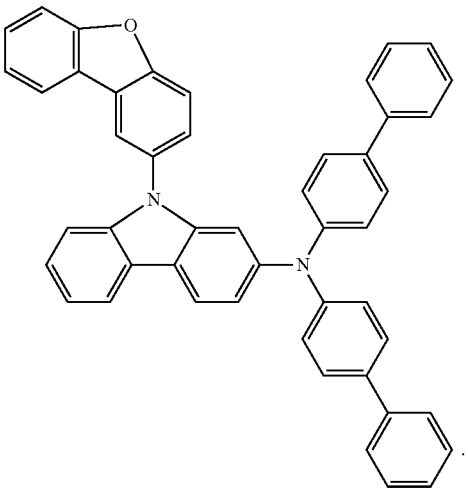 (B8)

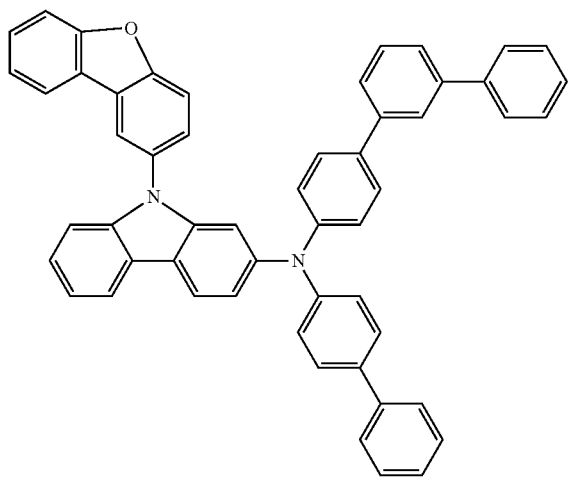 (B4)

2. A hole transport layer containing the amine compound as defined in claim 1.

3. A hole injection layer containing the amine compound as defined in claim 1.

4. A luminescent layer containing the amine compound as defined in claim 1.

5. An organic EL device containing the amine compound as defined in claim 1 in at least one of a luminescent layer, a hole transport layer and a hole injection layer.

6. An organic EL device containing the amine compound as defined in claim 1 in a hole transport layer.

* * * * *